United States Patent
Ntziachristos et al.

(10) Patent No.: US 7,804,075 B2
(45) Date of Patent: Sep. 28, 2010

(54) METHOD AND SYSTEM FOR TOMOGRAPHIC IMAGING USING FLUORESCENT PROTEINS

(75) Inventors: Vasilis Ntziachristos, Charlestown, MA (US); Jorge Ripoll, Heraklion (GR); Giannis Zacharakis, Heraklion (GR)

(73) Assignee: The General Hospital Corporation, Boston, MA (US)

( * ) Notice: Subject to any disclaimer, the term of this patent is extended or adjusted under 35 U.S.C. 154(b) by 285 days.

(21) Appl. No.: 10/598,703

(22) PCT Filed: Mar. 10, 2005

(86) PCT No.: PCT/US2005/007652

§ 371 (c)(1),
(2), (4) Date: Sep. 8, 2006

(87) PCT Pub. No.: WO2005/089637

PCT Pub. Date: Sep. 29, 2005

(65) Prior Publication Data

US 2007/0274580 A1    Nov. 29, 2007

Related U.S. Application Data

(60) Provisional application No. 60/552,249, filed on Mar. 11, 2004, provisional application No. 60/570,690, filed on May 13, 2004.

(51) Int. Cl.
*G01N 21/64* (2006.01)

(52) U.S. Cl. ............... 250/458.1; 250/252.1; 250/459.1

(58) Field of Classification Search ............. 250/458.1, 250/361 R, 362, 363.02, 363.04, 363.07, 250/367, 369, 368, 459.1, 461.1, 461.2
See application file for complete search history.

(56) References Cited

U.S. PATENT DOCUMENTS

| 5,787,887 A | 8/1998 | Klingenbeck-Regn |
| 7,242,997 B2 * | 7/2007 | Geng ......................... 700/117 |
| 2001/0037811 A1 | 11/2001 | Beuthan et al. |
| 2001/0055462 A1 * | 12/2001 | Seibel ........................ 385/147 |

(Continued)

FOREIGN PATENT DOCUMENTS

EP    0 336 208 A1    10/1989

(Continued)

OTHER PUBLICATIONS

European Search Report and Written Opinion for EP 0705199.5 dated Dec. 27, 2007.

(Continued)

*Primary Examiner*—David P Porta
*Assistant Examiner*—David S Baker
(74) *Attorney, Agent, or Firm*—Daly, Crowley, Mofford & Durkee, LLP

(57) ABSTRACT

A system for optical tomography includes an apparent light source adapted to project excitation light toward a specimen having fluorescent proteins therein, wherein the excitation light enters the specimen becoming intrinsic light within the specimen, wherein the intrinsic light is adapted to excite fluorescent light from the fluorescent proteins, and wherein the intrinsic light and the fluorescent light are diffuse. A method of optical tomography includes generating the excitation light with the apparent light source, wherein the intrinsic light and the fluorescent light are diffuse.

43 Claims, 16 Drawing Sheets

U.S. PATENT DOCUMENTS

| | | |
|---|---|---|
| 2002/0037252 A1 | 3/2002 | Toida |
| 2002/0089658 A1* | 7/2002 | Seville ........................ 355/113 |
| 2003/0124244 A1* | 7/2003 | Freeman et al. ................. 427/8 |
| 2003/0220549 A1 | 11/2003 | Liu et al. |
| 2004/0015062 A1 | 1/2004 | Ntziachristos et al. |

FOREIGN PATENT DOCUMENTS

| | | |
|---|---|---|
| EP | 336208 A1 * | 10/1989 |
| WO | WO 96/26431 | 8/1996 |
| WO | WO 02/41760 A2 * | 5/2002 |
| WO | WO 02/41760 A3 | 5/2002 |
| WO | WO 03/077750 A1 | 9/2003 |
| WO | WO 2004/008952 A1 | 1/2004 |
| WO | WO 2004/072906 A1 | 8/2004 |
| WO | WO 2004/113889 A1 | 12/2004 |
| WO | WO 2005/089637 A3 | 9/2005 |

OTHER PUBLICATIONS

PCT Search Report and Written Opinion of the ISA for PCT/US2005/007652 dated Nov. 14, 2005.

* cited by examiner

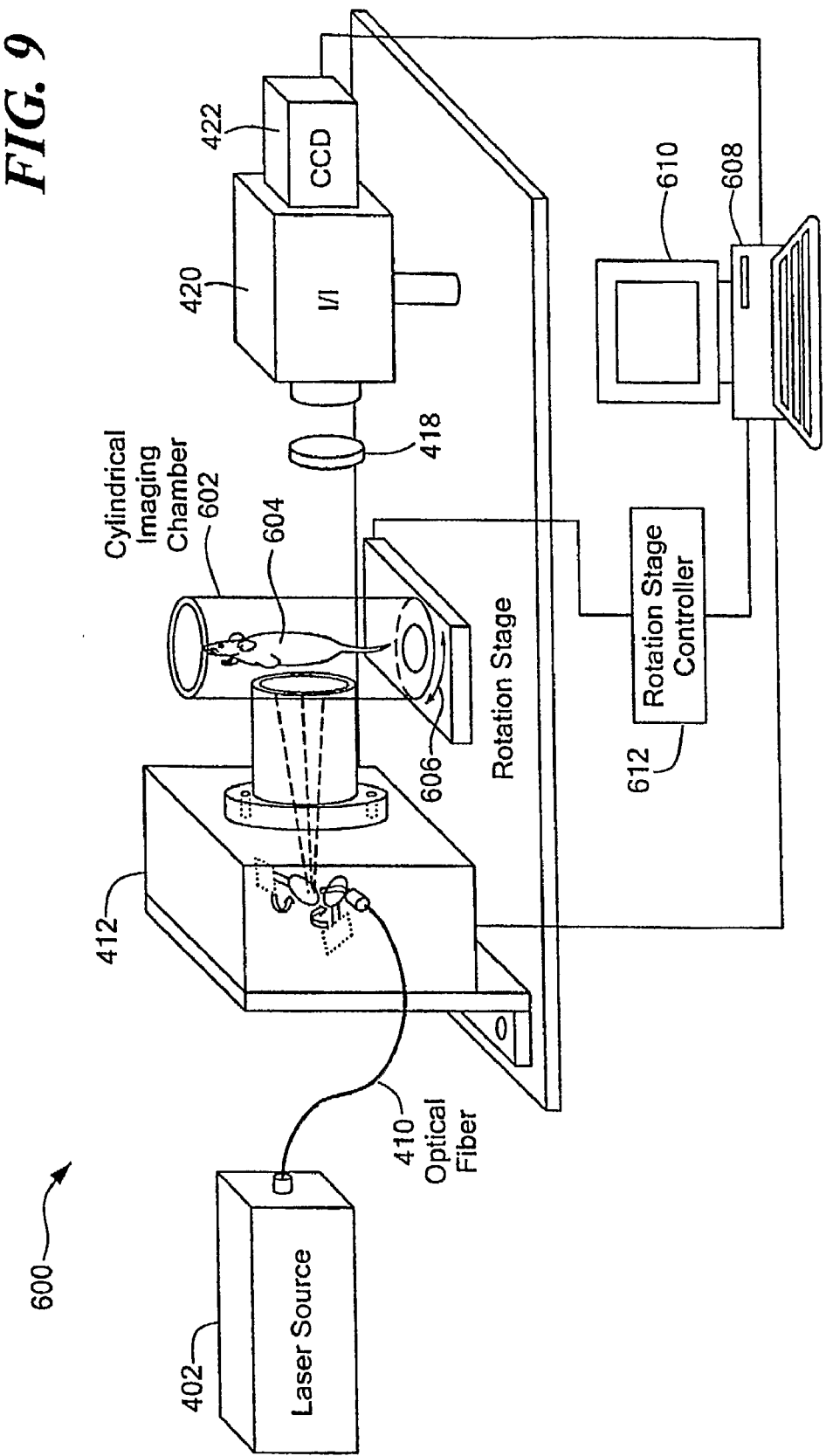

US 7,804,075 B2

METHOD AND SYSTEM FOR TOMOGRAPHIC IMAGING USING FLUORESCENT PROTEINS

CROSS REFERENCE TO RELATED APPLICATIONS

This application is a National Stage Application under 35 U.S.C. §371 of International Application number PCT/US2005/007652 filed on Mar. 10, 2005, published in the English language on Sep. 29, 2005 as International Publication Number WO2005/089637, and which claims the benefit under 35 U.S.C. §119(e) of U.S. Provisional Patent Application No. 60/552,249 filed on Mar. 11, 2004 and U.S. Provisional Patent Application No. 60/570,690 filed on May 13, 2004.

FIELD OF THE INVENTION

This invention relates generally to optical tomography and, more particularly, to a method and system for extracting quantitative, three-dimensional molecular and biological information from living specimens using fluorescent proteins.

BACKGROUND OF THE INVENTION

Fluorescent proteins (FPs) are important reporter molecules for different biomedical applications. In some existing applications, engineered FPs are detected by epi-fluorescence, confocal (microscopy), or reflectance (whole animal) imaging.

Epi-fluorescence, confocal microscopy depends on coherent (non-diffuse) light projected toward and reflected from a specimen. Because microscopy requires substantially coherent light, this technique is only able to image to a small depth (e.g., less than 1 mm) into the specimen. At deeper imaging depths, light is known to become diffuse, rendering microscopy ineffective at the deeper imaging depths.

Reflectance fluorescence imaging has been shown to be useful in detecting and following tumors in vivo, particularly those implanted near the surface or in surgically exposed organs. However, reflectance fluorescence imaging has inherent limitations, since obtained images are a superposition of fluorescence signals from multiple depths, which tends to result in blurred images. Furthermore, reflectance fluorescence imaging is not tomographic and does not retrieve depth information or allow absolute quantification of fluorescence activity. This is due in part to non-linear light attenuation and propagation in biological tissues, which limits the applicability of reflectance fluorescence imaging to semi-quantitative imaging at depths of only a few millimeters.

Imaging optical signatures deeper in tissues often requires the application of advanced light excitation and light detection apparatus and techniques and the use of tomographic principles for combining data acquired at different projections. Advances in imaging with diffracting light sources have resulted in several studies investigating tissue using intrinsically or extrinsically administered optical contrast. In particular, diffuse optical tomography (DOT) is a technique that can provide a tomographic image associated with a diffuse media in the presence of absorption and scattering in the diffuse media. For example, DOT has been applied to cerebral hemodynamic imaging and imaging of breast tissue. One exemplary DOT method and system is described, for example, in international patent application PCT/US04/03229, by Vasilis Ntziachristos and Jorge Ripoll, entitled "Method and System for Free Space Optical Tomography of Diffuse Media," filed Feb. 5, 2004, which application is assigned to the assignee of the present invention.

It has been shown that light with wavelengths in the near-infrared range can propagate through tissue for distances on the order of several centimeters because of low tissue absorption in the so-called "near-infrared window." The near-infrared (NIR) window has enabled the development of NIR fluorescence techniques to visualize specific biochemical events inside living specimens.

A variety of related methods for processing NIR fluorescent signals have also been developed. In particular, development of appropriate imaging systems has enabled the application of Fluorescence Molecular Tomography (FMT), a technique that resolves molecular signatures in deep tissues using NIR fluorescent probes or markers. FMT used for in vivo three-dimensional imaging of enzymatic activity in deep-seated tumors has been demonstrated.

A common assumption in conventional NIR optical tomography is that propagation in a diffuse media has high scattering but relatively low absorption, as provided by the NIR window. This assumption has allowed derivation of a "diffusion equation" associated with a "transport equation," by means of a "diffusion approximation," which provides an effective tool for modeling NIR photon propagation in tissues. The transport equation is described, for example, in K. M. Case and P. F. Zweifel, "Linear Transport Theory," Addison-Wesley, Mass., (1967) and in K. Furutsu and Y. Yamada, "Diffusion Approximation for a Dissipative Random Medium and the Applications," Phys. Rev. E 50, 3634 (1994).

As is known, all currently available fluorescent proteins utilize excitation light having a wavelength in the visible range. Moreover, conventional fluorescent proteins emit visible fluorescent light when excited. Tomographic imaging using visible light, as provided by the conventional fluorescent proteins, is complicated by a relatively high absorption of visible light propagating in biological tissue, which results in significant attenuation. With high absorption, (e.g., for visible light) the conventional diffusion approximation described above is not valid.

Other, more advanced solutions (other than the above-described diffusion approximation) to the transport equation have been generated and applied to NIR optical tomography. The advanced solutions overcome the inadequacy of the above-mentioned diffusion approximation. However the advanced solutions to the transport equation are generally computationally expensive and become impractical for tomographic systems having a large number of excitation light sources, resulting in large data sets.

In order to provide a plurality of images necessary for tomography, many conventional optical tomography systems use an optical switch as part of a light source assembly in order to use a single light element to project at a variety of angles or positions relative to a specimen. It is known that the optical switch generates energy losses. Furthermore, many optical tomography systems use a CCD camera at room temperature or at moderate cooling to collect light. It is known that a room temperature or moderately cooled CCD camera exhibits a relatively high level of dark (thermal) noise, which tends to limit the quality of resulting optical tomography images.

SUMMARY OF THE INVENTION

In accordance with an aspect of the present invention, a system for optical tomography includes an apparent light source adapted to project excitation light toward a specimen having fluorescent proteins therein, wherein the excitation light enters the specimen becoming intrinsic light within the specimen. The intrinsic light is adapted to excite fluorescent light from the fluorescent proteins. The intrinsic light and the fluorescent light are diffuse. In some embodiments, at least one of the excitation light and the fluorescence light has a wavelength in the visible wavelength range.

In accordance with another aspect of the present invention, a method of optical tomography includes generating excitation light with an apparent light source adapted to project the excitation light toward a specimen having fluorescent proteins therein, wherein the excitation light enters the specimen becoming intrinsic light within the specimen. The intrinsic light is adapted to excite fluorescent light from the fluorescent proteins. The intrinsic light and the fluorescent light are diffuse. In some embodiments, at least one of the excitation light and the fluorescent light has a wavelength in the visible wavelength range.

In accordance with another aspect of the present invention a system for optical tomography includes at least one selectively movable component to selectively move an apparent light source to direct a plurality of light paths toward a specimen.

BRIEF DESCRIPTION OF THE DRAWINGS

The foregoing features of the invention, as well as the invention itself may be more fully understood from the following detailed description of the drawings, in which:

FIG. 9 is a block diagram of another alternate system for optical tomography having a rotating cylindrical imaging chamber;

DETAILED DESCRIPTION OF THE INVENTION

Figure 1:
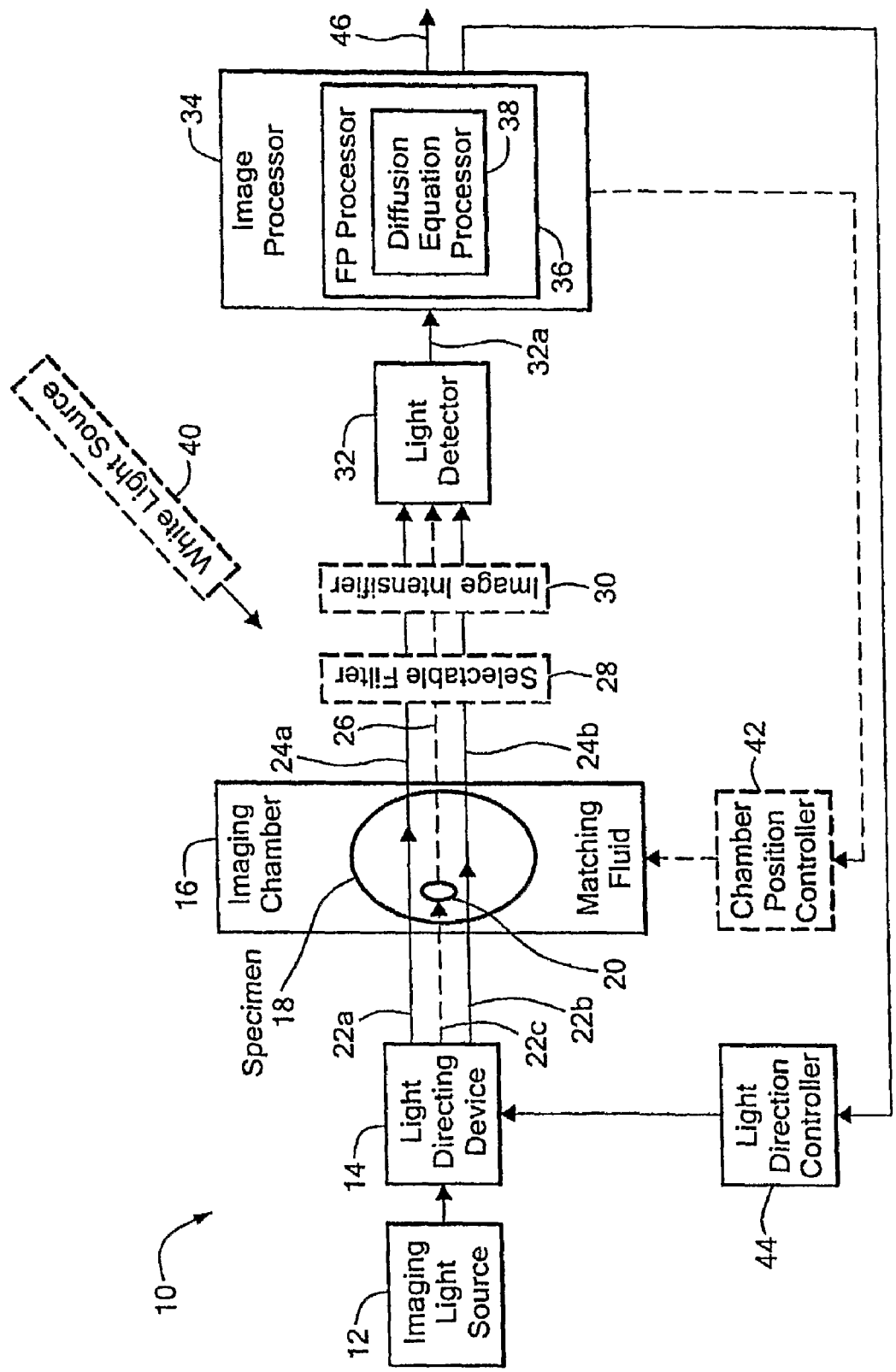
FIG. 1 is a block diagram showing a system for optical tomography, which provides transillumination imaging.

Before describing the imaging method and system, some introductory concepts and terminology are explained. As used herein, a "phantom" refers to a test object being imaged. A phantom is typically a manufactured article having diffuse light propagation characteristics similar to living tissue, for example, a piece of plastic. For another example, a phantom can be a vial having cells expressing the fluorescent proteins therein, i.e. a fluorescent marker.

As used herein, the term "apparent light sources" is used to describe projections of a single light source to a plurality of physical positions or angles, each providing an apparent light source.

As used herein, the term "excitation" light is used to describe light generated by an excitation light source, (for example, an apparent light source) that travels toward a specimen to be imaged, before entering the specimen. Once in the specimen, the light is referred to herein as "intrinsic" light. The intrinsic light is subject to absorption and scattering in the specimen and can also exit the specimen.

The intrinsic light, having exited the specimen, is at the same wavelength at which it was generated by the excitation light source. The excitation and intrinsic light can be monochromatic or they can cover a broader spectrum, for example, as white light.

In some embodiments, the intrinsic light exiting the specimen is received by a light detector device disposed generally on the same side of the specimen as the light source (for example, in reflectance imaging of FIG. 1A described below). In other embodiments, the intrinsic light exiting the specimen is received by a light detector disposed generally on the opposite side of the specimen as the excitation light source, after it passes through the specimen (for example, in transillumination imaging of FIG. 1 described below). In either case, the excitation light becomes intrinsic light when it enters the specimen and either reflects from the inside of the specimen or passes through the specimen.

As used herein, the terms "emitted" light is used to describe light generated by or within a biological tissue. As used herein, the term "fluorescence" or "fluorescent" light is used to describe a form of emitted light generated via excitation of a fluorescent protein in response to the intrinsic light.

As used herein, the term "image" is used to describe a visual representation having underlying "image data" generated by a digital camera or by a computer system. However, it will be understood that the term "image," as used herein, is also used to refer to the image data.

As used herein, the term "diffuse" is used to describe light having photons that have encountered several scattering events (for example, more than ten scattering events) when propagating inside a specimen, independent of absorption of the photons in the specimen. The number of scattering events can be more than or less then ten.

The method and system of the present invention are described below to apply to visible light propagating in a biological tissue for which diffuse light propagation dominates. However, the method and system apply equally well to any form of light propagating in any medium for which diffuse propagation dominates, for example, NIR light propagating to a distance sufficiently deep in biological tissue, for example, visible excitation light and NIR fluorescent (emitted) light. Also, the method and system can also be applied to light propagating in a medium for which coherent propagation dominates.

While the method and system of the present invention are described herein as applied to fluorescent proteins that emit visible fluorescent light, providing particular benefits in the visible wavelength range of about 400 nm to 700 nm, the method and system can also be applied to light having other wavelengths, for example to fluorescent light in the near infra red (NIR) range of about 700 nm to 1000 nm. Also, the method and system apply equally well to a system in which excitation light is in one wavelength range, for example, in the visible range, and the fluorescent light emitted by the fluorescent proteins is in another wavelength range, for example in the NIR range. The method and system also apply where both the excitation light and the fluorescent light emitted by the fluorescent proteins are in the NIR range or both are in the visible range. Also, light beyond the wavelength range of 400 nm to 1000 nm can be used.

Referring to FIG. 1, a system 10 for optical imaging using fluorescent proteins includes an imaging light source 12 and a light directing device 14 to provide a plurality of apparent light sources (not shown). The apparent light sources provide excitation light 22a-22c at a variety of positions relative to a specimen 18. While three such positions are shown, there can be more than three or fewer than three apparent light source positions. The excitation light 22a, 22c impinges upon the specimen 18, becoming intrinsic light upon entry, and exits the specimen 18 as intrinsic light 24a, 24b. The intrinsic light 24a, 24b passes through an optional selectable light filter 28, through an optional image intensifier 30, and is received by a light detector 32. The excitation light 22b also passes into the specimen 18 and impinges upon fluorescent proteins 20 within the specimen 18. In response to the excitation light 22b the fluorescent proteins 20 emit fluorescent light 26, which also passes through the optional selectable light filter 28, through the optional image intensifier 30, and is received by the light detector 32.

An optional white light source 40 can provide further illumination of the specimen, to provide other light paths (not shown), which reflect from a surface of the specimen, and which also pass through the optional selectable light filter 28, through the optional image intensifier 30, and are received by the light detector 32.

In some embodiments, the intrinsic light 24a, 24b, the fluorescent light 26, and the white light from the white light source 40 are simultaneously received by the light detector. In this arrangement, the intrinsic light 24a, 24b, the fluorescent light 26, and the white light from the white light source 40 can be separated by the selectable filter 28, to provide the different lights to the light detector 32 at the same time or at separate times. To this end, the selectable filter passband can be centered at different times on the wavelength of the intrinsic light, the fluorescent light, and the white light.

In other embodiments, any one or more of the intrinsic light 24a, 24b, the fluorescent light 26, and the white light from the white light source 40 are received at different times than other ones of the intrinsic light 24a, 24b, the fluorescent light 26, and the white light from the white light source 40. For example, in one particular embodiment, the intrinsic light 24a, 24b is received first, at which time, the imaging light source 12 is extinguished. The fluorescent light 26 is received after the intrinsic light 24a, 24b is no longer present. After the fluorescent light 26 stops being emitted, the white light source 40 is turned on, and the white light is received.

The light detector 32 operates to convert the received light into digital data 32a (also referred to herein as image data). An image processor 34 receives the digital data 32a and generates an image 46. In some embodiments, the image 46 is a tomographic image.

The image processor 34 can include a forward problem (FP) processor 36 having a diffusion equation processor 38. Functions of the forward problem processor 36 and the diffusion equation processor 38 are described more fully below, for example, in conjunction with FIG. 4. Let it suffice here to say that the forward problem processor 36 compares a model of light propagation in the specimen (expected light) with the light received by the light detector. A difference between the received light and the expected light (provided by a light propagation model) is associated with the fluorescent proteins 20 within the specimen. The diffusion equation processor 38 provides a modified diffusion coefficient used in a "diffusion equation" associated with a "transport equation" that can be used to provide the above-described light propagation model.

In some embodiments, the modified diffusion coefficient allows the model to predict light propagation for light in the visible wavelength region, having a wavelength of about 400 nm to 700 nm. In other embodiments, the modified diffusion coefficient allows the model to predict light propagation for light in the near infrared wavelength region, having a wavelength of about 700 nm to 1000 nm. In still other embodiments, the modified diffusion coefficient allows the model to predict light propagation for light having a wavelength outside of the range of 400 nm-1000 nm The system 10 can also include a light direction controller 44 to direct the apparent light sources to predetermined light paths. The system 10 can also include an optional chamber position controller 42 in place of or in combination with the light direction controller 44 that can be used to move an imaging chamber 16 to provide more apparent light sources, i.e., the intrinsic light passes through the specimen 18 along more predetermined light paths.

It should be appreciated that the system 10 provides a transillumination imaging system for which light generated by the imaging light source 12 passes through the specimen 18 and is received essentially on the other side of the specimen 18.

Figure 1A:
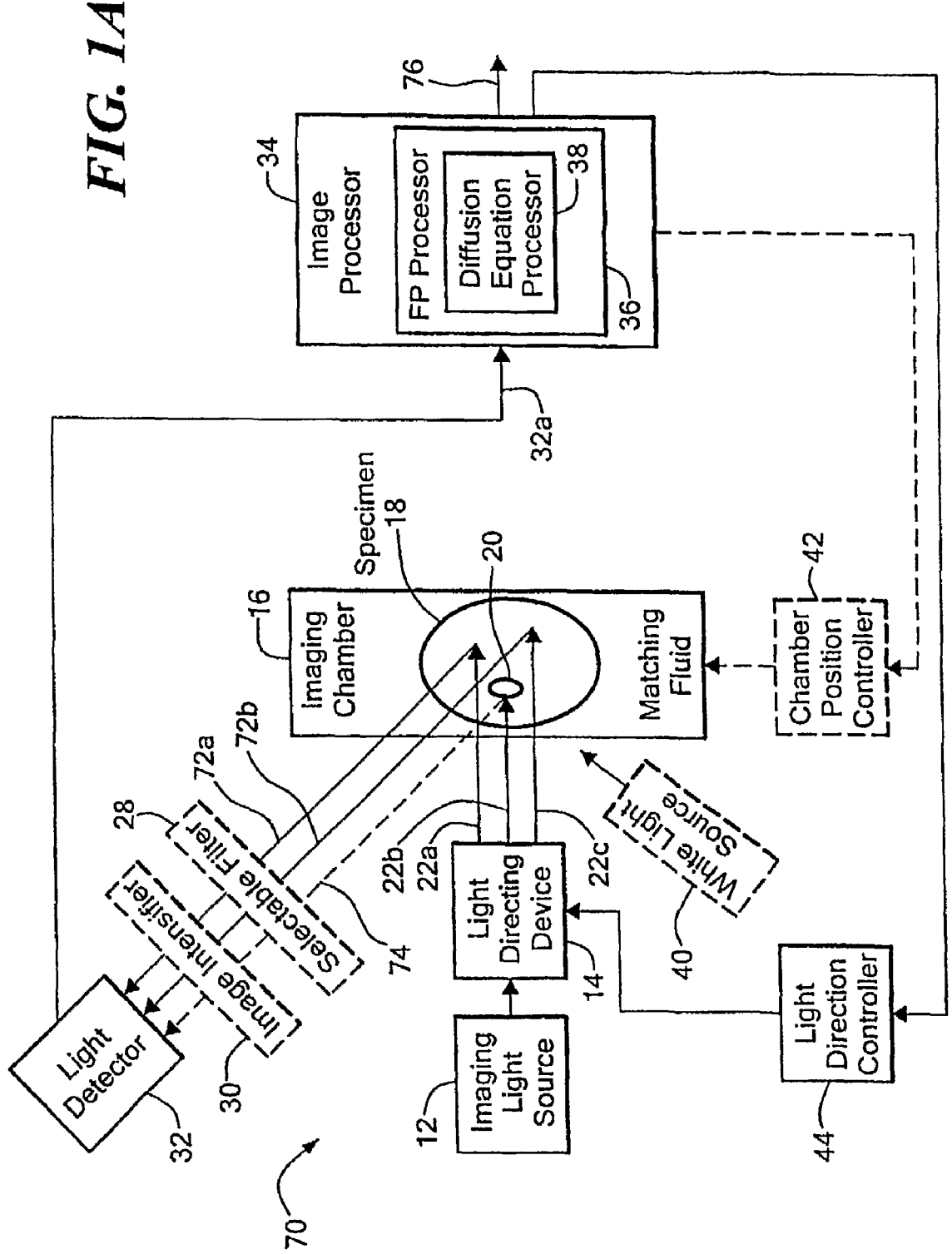
FIG. 1A is a block diagram showing a system for optical tomography, which provides reflectance imaging.

Referring now to FIG. 1A, a system 70, for which like element of FIG. 1 are shown having like reference designations, the selectable filter 28, the image intensifier 32, and the light detector 32 are positioned generally on the same side of the specimen 18 as the imaging light source 12 and the light directing device 14. With this particular arrangement, intrinsic light 72a, 72b is received by the light detector 32 as reflected light. Essentially, the excitation light 22a-22c passes into the specimen 18 and reflects, or more specifically, scatters, back to the light receiver 32. Fluorescent light 74 is also received by the light detector 32. The system 70 generates an image 76.

It should be appreciated that the system 70 provides a reflectance imaging system for which light emitted by the imaging light source 12 passes into the specimen 18 and is received essentially on the same side of the specimen 18. In other embodiments, an angle between the light directing device 14 and the light detector 32 is approximately ninety degrees.

Figure 2:
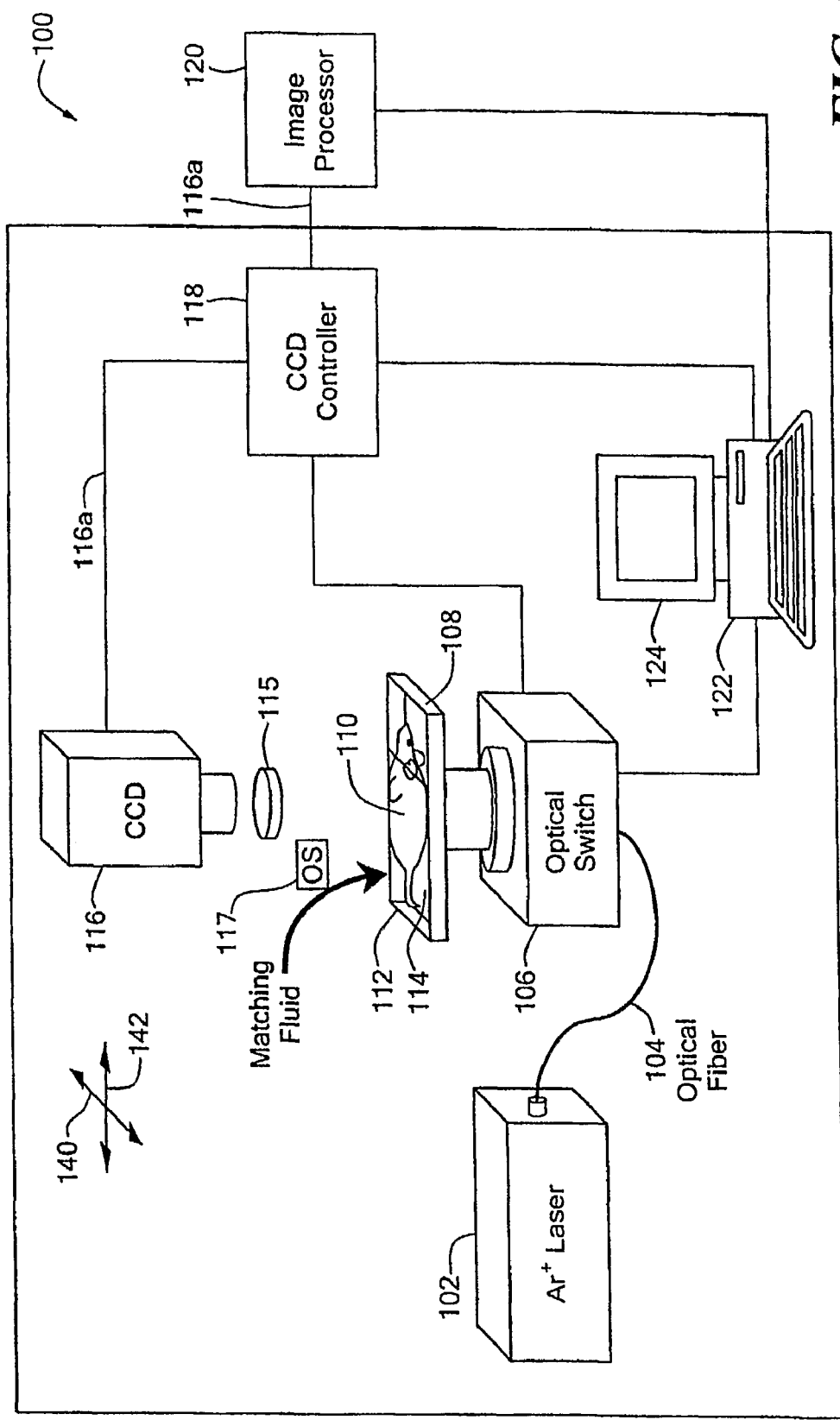
FIG. 2 is a block diagram showing a system for optical tomography having a laser source, an optical fiber, an optical switch, a cooled CCD camera, and an image processor.

Referring now to FIG. 2, an apparatus 100 includes a laser 102, an optical fiber 104, and an optical switch 106, which, in combination, generate a plurality of apparent light sources directed toward an imaging chamber 112 having an imaging plate 108 upon which a specimen 110 is placed. The imaging chamber can be filled with a matching fluid 114. A selectable filter 115 and a CCD camera 116 receive intrinsic light passing through the specimen 110 and fluorescent light emitted by the specimen 110. As described above, the selectable filter has a passband selectively centered on a wavelength of the intrinsic light or the fluorescent light, depending upon whether an intrinsic image or a fluorescence image is being generated. The optical switch 106 can be controlled by a computer 122. The computer 122 can also control the CCD camera 116 via a CCD controller 118. An image processor 120 receives digital data 116a via the CCD controller 118. A graphical display 124 can display resulting image information.

It should be recognized that the laser 102 corresponds to the imaging light source 12 of FIGS. 1 and 1A, the optical switch 106 corresponds to the light directing device 14 of FIGS. 1 and 1A, the imaging chamber 112 corresponds to the imaging chamber 16 of FIGS. 1 and 1A, the CCD camera 116 corresponds to the light detector 32 of FIGS. 1 and 1A, and the image processor 120 corresponds to the image processor 34 of FIGS. 1 and 1A.

The specimen 110 is shown here to be a mouse placed in the imaging chamber 112. The laser 102 provides excitation light (not shown), which enters the specimen 110 and excites fluorescent proteins (not shown) within the specimen 110 to generate fluorescent light (not shown). The CCD camera 116 receives the laser light as intrinsic light (having passed through the specimen 110) and also receives the fluorescent light emitted from within the specimen 100 via the selectable filter 115.

In one particular embodiment, the laser 102 is an Argon (Ar$^+$) laser emitting laser light at approximately 200 mW continuous wave (CW) power having a wavelength of approximately 488 nm. The laser light can be used to excite the fluorescent proteins within the specimen 110, for example, green or yellow fluorescent proteins.

In one particular embodiment, the optical fiber 104 is a 100 μm diameter multimode optical fiber. The laser 102 provides a plurality of apparent light sources at different physical positions relative to the specimen 110 by way of the optical switch 106. In one particular embodiment, the optical switch provides thirty-one apparent light sources. However, in other embodiments, more than thirty-one or fewer than thirty-one apparent light sources can be provided.

Figure 3:
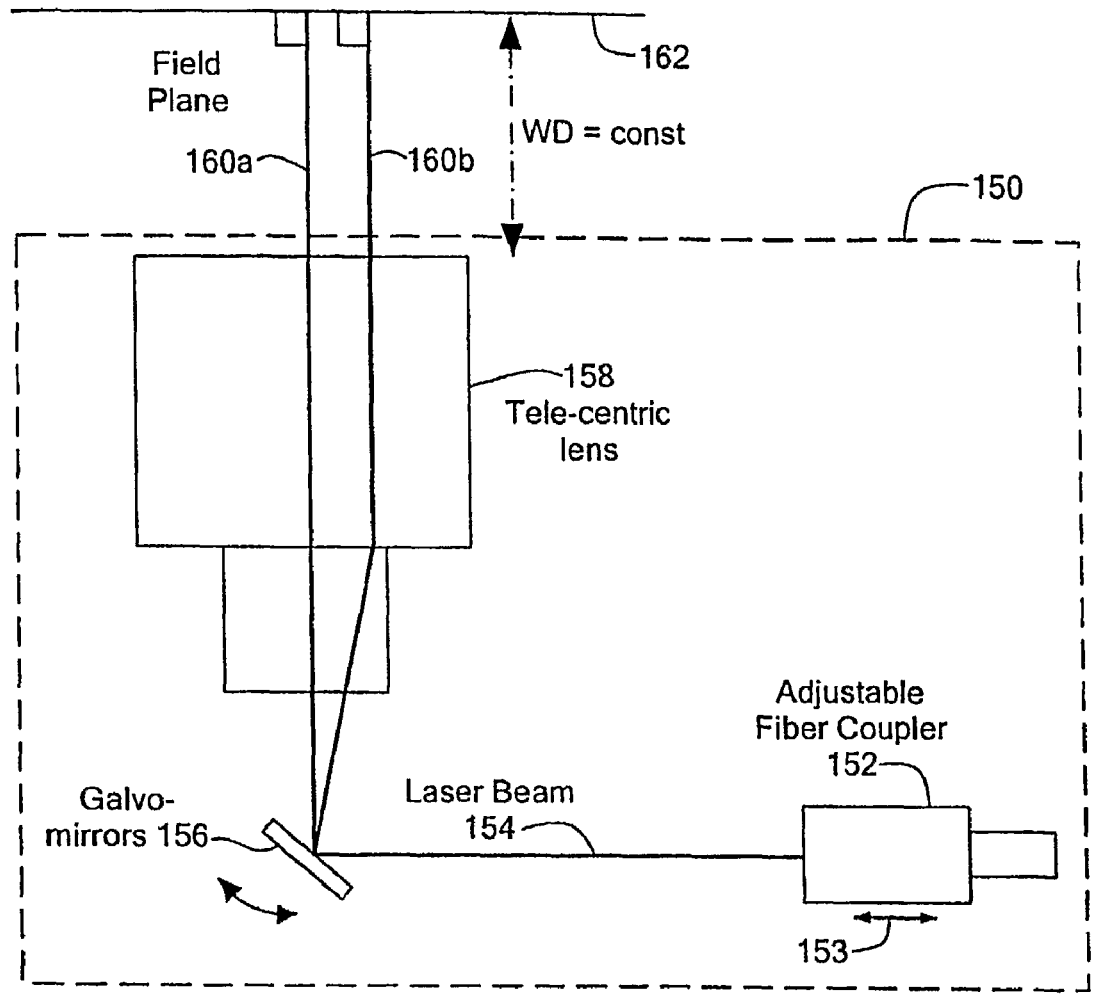
FIG. 3 is a block diagram of an optical scanner having a fiber coupler, a position-controlled mirror, and a telecentric lens, together used for generation of a plurality of apparent light sources having a flat light field at a constant working distance (WD)

Though the optical switch 106 is shown, in another embodiment, the optical switch 106 can be replaced with an optical scanning head (or optical scanner), shown in greater detail in FIG. 3.

The optical switch 106 provides apparent light sources at a variety of angles or positions relative to the specimen 110, thereby allowing the image processor 120 to form a corresponding variety of images, which can be combined in a tomographic process by the image processor 120.

It will be understood that the optical switch 106 includes a plurality of selectable optical fiber paths (not shown), adapted to direct light to a corresponding plurality of selectable fixed physical locations, providing apparent light sources that are selectively fixed in position and number.

In one particular embodiment, living tissue, here shown to be a mouse, is placed on the imaging plate 108, in contact with the optical matching fluid 114. The matching fluid 114 is further described below. The matching fluid is used to reduce the affect of stray light. However, in other embodiments, no matching fluid is used.

Figure 4:
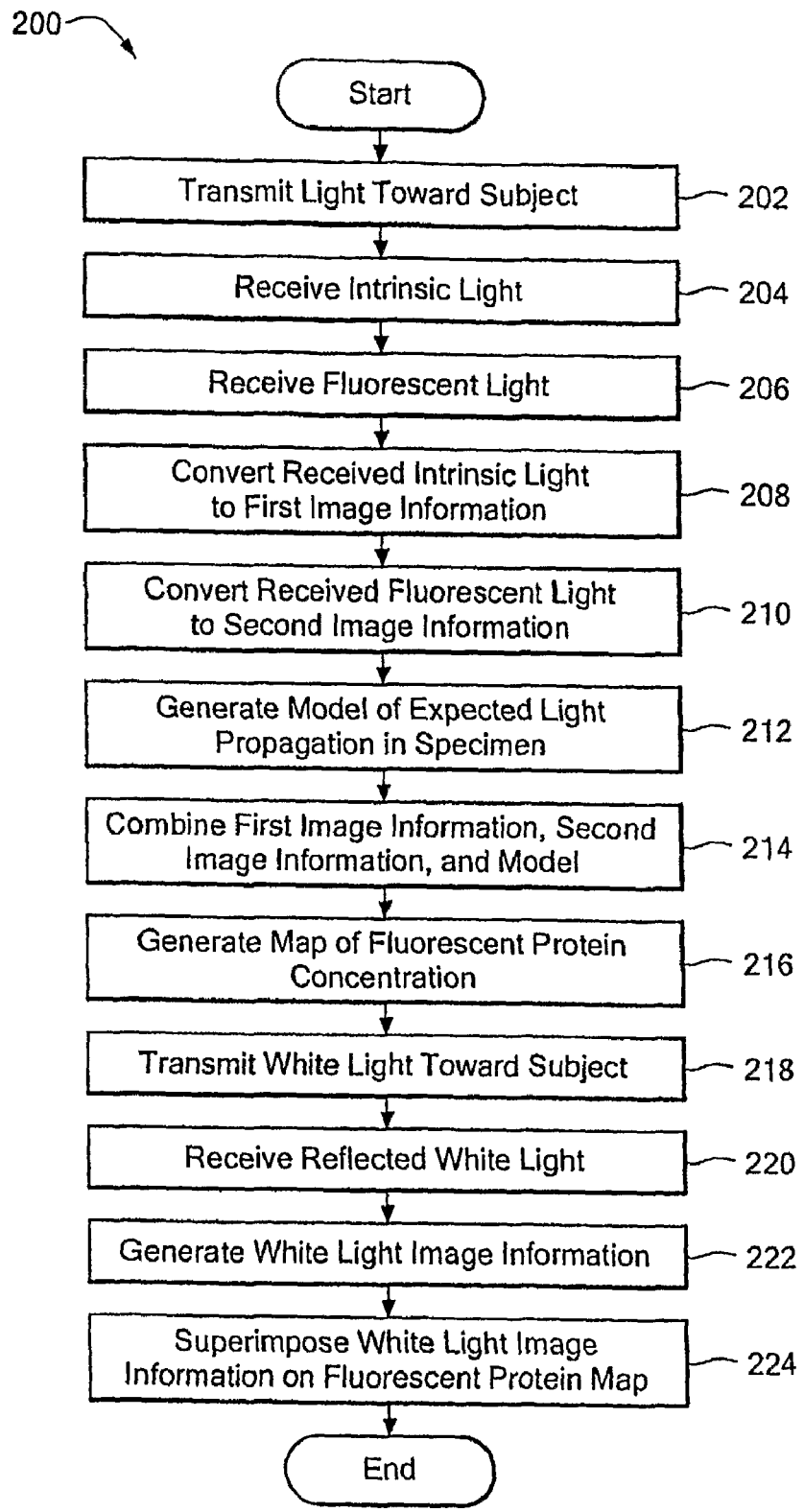
FIG. 4 is a flow chart showing a process used to provide a tomographic image in accordance with the present invention.

In operation, intrinsic light (originating from each of the apparent light sources) and also light emitted by fluorescent proteins within the specimen 110 are received by a CCD camera and thereafter tomographically processed by the image processor 120, for example, as described in conjunction with FIG. 4.

In one particular embodiment, the CCD camera 116 is a cooled CCD camera having reduced dark noise. For example, the CCD camera 116 can be provided as a Roper Scientific, Princeton Instruments CCD camera with a cryogenic cooling unit.

During operation, the optical switch 106 is controlled and triggered by the CCD controller 118 so that each obtained image corresponds to a new position of a new apparent light source (i.e., a different light path in the optical switch 106), thus achieving the proper synchronization of excitation and detection. Each acquisition is composed of N images, one acquisition for each apparent light source position. Therefore, assuming a 512×512 pixel CCD camera, a maximum number of data for each set of measurements is N×512×512. However, the number of detectors (i.e., pixels) used for the subsequent processing by the image processor 120 can be smaller than the fall group of 512×512 pixels, depending on the field of view associated with each of the apparent light sources. Also, the number of pixels used can be reduced to reduce computational time required for image processing.

In one particular embodiment, the CCD camera 116 and the selectable filter 115 are selectively movable, for example, in directions represented by arrows 140, 142 about the specimen 110 in order to achieve more images at other angles relative to the specimen 110. In yet another embodiment, an optical scanner 117, somewhat offline from the CCD camera 116, can provide images at other angles relative to the specimen.

The specimen 110 can be placed horizontally on the imaging plate 108 and compressed with a covering glass (not shown). The imaging chamber 112 is then filled with the matching fluid 114, which, in one particular embodiment, is comprised of an intralipid and India ink solution. The matching fluid 114 provides a match of optical properties, which tends to reduce the index of refraction and diffuse-wave mismatches in the chamber. In one particular embodiment, the matching fluid 114 is comprised of 1% intralipid and 2.1% ink, which corresponds to $\mu_a=1.25$ cm$^{-1}$ and $\mu_s'=16.7$ cm$^{-1}$ where $\mu_a$ is an absorption coefficient and $\mu_s'$ is a reduced scattering coefficient, respectively. The reduced scattering coefficient is further described below.

Referring now to FIG. 3, an optical scanner 150 can be used in place of the optical switch 106 of FIG. 2 and can also be used as the optical scanner 117 of FIG. 2. In one particular embodiment, the optical scanner 150 can include two galvanometer controlled mirrors (here one galvanometer controlled mirror 156 is shown for clarity), pivoting about generally orthogonal axes, and a scan lens 158 to scan and focus a laser beam 156 onto an input window of an imaging chamber 162 to provide a plurality of apparent light sources, each at a different physical position, here represented by light beams 160a and 160b. In one particular embodiment, the scan lens 158 is a telecentric lens. In one particular embodiment, a light beam diameter at a field plane 162 (e.g., imaging chamber 112 of FIG. 2) is approximately 300 μm. A single light source (not shown) can be used, which is received by a fiber coupler 152.

The optical scanner 150 provides less optical loss compared to optical losses of a conventional optical switch, e.g., the optical switch 106 of FIG. 2. Thus, the optical scanner 150 provides a lower loss apparent light source system. Furthermore, with the optical scanner 150, a scanning area, a light beam shape, as well as a number of apparent light sources and apparent light source positions can be substantially infinitely varied, unlike the optical switch 106 of FIG. 2, for which a fixed number of light paths are in fixed positions. Also, a higher light power and a wider light wavelength range (visible light to near infrared (NIR) light) can be achieved.

The optical scanner 150 has a variety of advantages over an optical switch, including, but not limited to, lower energy losses, uniform response over a number of apparent light sources, and improved reliability and robustness. Also, a scanning area as well as a number and spatial configuration of the apparent light sources can be software controlled and can, therefore, be varied in accordance with characteristics of the specimen being scanned. Furthermore, higher power illumination and a wider wavelength range (e.g., from 400 to 1000 nanometers) can be achieved.

Referring now to FIG. 4, a method 200 of optical tomography begins at step 202, where excitation light is generated and transmitted toward a specimen. In some embodiments, for example, embodiments resulting in a tomographic image, the excitation light is provided from a plurality of apparent light sources corresponding to different positions relative to the specimen.

In some embodiments, the plurality of light sources provides excitation light generally simultaneously at the plurality of apparent light sources. In other embodiments, the plurality of apparent light sources provides excitation light sequentially.

At block 204, intrinsic light is received. As described above, the intrinsic light corresponds to the excitation light having passed into and out of the specimen. The intrinsic light can be received with a light detector, for example, the light detector 32 of FIG. 1. In some embodiments the received intrinsic light corresponds to transillumination light, wherein the light detector and the apparent light sources are essentially on opposite sides of the specimen. In other embodiments the received intrinsic light corresponds to reflectance light, wherein the light detector and the apparent light sources are essentially on the same side of the specimen.

At block 206, fluorescent light is received. The fluorescent light is emitted by fluorescent proteins within the specimen in response to the intrinsic light. The fluorescent light can be received with a light detector, for example, the light detector 32 of FIG. 1. In some embodiments, the fluorescent light and the intrinsic light are received at the same time, for example, by way of optical filters (e.g., 28, FIG. 1) adapted to separate the fluorescent light from the intrinsic light. In other embodiments, the fluorescent light is received after the excitation light is extinguished, also by way of an optical filter.

At block 208, the received intrinsic light is converted to first image information, for example, digital data 32a of FIG. 1. At block 210, the received fluorescent light is converted to second image information, which can also be digital data 32a.

At block 212, a model is generated to predict light propagation in the specimen. The model can be based on the diffusion equation having a modified diffusion coefficient as described more fully below, for example, as in Eq. (4) below and having a modified wave number as in Eq. (6) below.

The optical model generated at block 212 can be associated with propagation in a homogenous medium, i.e. a medium that has no optical heterogeneity. In other embodiments, more advanced models can be also utilized to resolve and then employ information on background optical heterogeneity.

It will become apparent from the discussion below, that light propagation in tissues can be modeled by using the modified diffusion equation having a modified diffusion coefficient, wherein the modified diffusion coefficient is adapted to predict characteristics of light propagation for a diffuse medium in which the medium has relatively high absorption, as for example, in cases of visible light propagating in biological tissue. Having the modified diffusion coefficient described below, the modified diffusion equation can predict, for example, the propagation of visible light in biological tissue, which is known to be diffuse and have relatively high absorption of visible light. However, the modified diffusion equation is also suited to accurately predict the propagation of light having other wavelengths traveling in a diffuse medium, for example, near infrared light propagating in biological tissue.

The general diffusion equation can be derived from a Radiative Transport Equation. Both the intrinsic light field, which is generated by the laser excitation light (intrinsic light) propagating inside the medium, and the fluorescent light field, which is generated inside the medium due to a fluorescent protein at a position $\vec{r}$, are calculated independently and then used to calculate a normalized Born field (the diffusion approximation). As described more fully below, a modified diffusion equation can be used in forward problem to provide an image of the fluorescent proteins inside the medium.

A Born field $U_c(\vec{r}_s, \vec{r}_d)$ for light propagating in a medium as detected at the light detector position $\vec{r}_d$ due to an apparent light source at position $\vec{r}_s$ having both a modified diffusion coefficient and modified propagation wave numbers, that both account for high absorption is given by:

$$U_c(\vec{r}_s, \vec{r}_d) = S_o \frac{U_{fl}(\vec{r}_s, \vec{r}_d) - \Theta_f U_{inc}(\vec{r}_s, \vec{r}_d)}{U_{inc}(\vec{r}_s, \vec{r}_d)} = \frac{1}{U_o(\vec{r}_s - \vec{r}, k^{\lambda_1})} \int d^3 r \cdot U_o(\vec{r}_s - \vec{r}, k^{\lambda_1}) n(\vec{r}) \frac{v}{D^{\lambda_2}} G(\vec{r}_d - \vec{r}, k^{\lambda_2}) \quad (1)$$

where $U_{inc}(\vec{r}_s, \vec{r}_d)$ and $U_{fl}(\vec{r}_s, \vec{r}_d)$, are measurements at excitation ($\lambda_1$) (laser) and emission ($\lambda_2$) (fluorescent) wavelengths, respectively, $U_{bl}(\vec{r}_s, \vec{r}_d) = \Theta_f U_{inc}(\vec{r}_s, \vec{r}_d)$ is a bleed through signal, $\Theta_f$ is a band-pass filter attenuation factor associated, for example, with the selectable filter 28 of FIG. 1, $S_o$ is a gain term that accounts for instrument gain differences (e.g., light detector gain differences) at the excitation ($\lambda_1$) and emission ($\lambda_2$) wavelengths, $n(\vec{r})$ is a product of a fluorescent protein absorption coefficient and fluorescence quantum yield, $k^{\lambda_1} k^{\lambda_2}$ are modified photon wave propagation wave numbers at $\lambda_1$ and $\lambda_2$ respectively which account for high absorption, $v$ is the speed of light in the medium, $D^{\lambda_2}$ is the modified diffusion coefficient in the presence of the high absorption at $\lambda_2$, $U_0(\vec{r}_s - \vec{r}, k^{\lambda_2})$ is a term that describes the established photon field at position $\vec{r}$ in the medium at $\lambda_1$, and $G(\vec{r}_d - \vec{r}, k^{\lambda_2})$ is the Green's function solution to the diffusion approximation that describes the propagation of the emission photon wave from a fluorescent protein at position $\vec{r}$ to the light detector. The function $G(\vec{r}_d - \vec{r}, k^{\lambda_2})$ is given by:

$$G(\vec{r}_d - \vec{r}, k^{\lambda 2}) = \frac{\exp(ik^{\lambda 2}(\vec{r}_d - \vec{r}))}{(\vec{r}_d - \vec{r})} \quad (2)$$

Equation (1) above is essentially normalized by $U_{inc}$. An advantage of using the normalization in equation (1) is that position-dependent contributions are eliminated, and also, this field can be calculated even with the presence of the fluorescent proteins. This means that no background measurements are necessary before the administration of the fluorescent protein, which is important for in vivo studies.

A useful way to represent the absorption dependence of the diffusive light propagation independently of medium absorption is by writing the diffusion coefficient as:

$$D_\alpha = \frac{1}{3(\mu'_s + \alpha\mu_a)} \quad (3)$$

where $\alpha$ is a constant generally depending on the absorption, scattering, and anisotropy of the medium. The coefficient $\mu'_s$ is the reduced scattering coefficient, and $\mu_a$ is the absorption coefficient. The reduced scattering coefficient $\mu'_s$ can be written as $\mu'_s = (1-g)\mu_s$, where $\mu_s$ is the scattering coefficient. An expression for a modified diffusion coefficient $D_\alpha$ that accounts for high absorption may be found through derivation from the Radiative Transport Equation, obtaining:

$$D_\alpha = \frac{1}{3(\mu'_s + \mu_a)}\left(1 - \frac{4}{5}\frac{\mu_a}{\mu'_s(1+g) + \mu_a}\right)^{-1} \quad (4)$$

where g is an anisotropy factor. Here, $D_\alpha$ is expressed in terms of the reduced scattering coefficient $\mu'_s$, which is a relevant quantity in scattering experiments in anisotropic media. One main difference between Eq. (4) and most commonly used expressions for the standard diffusion coefficient D is that in the commonly used expressions the value of $\alpha$ is fixed a-priori to $\alpha=0$ or $\alpha=1$. A more generic expression of $\alpha$ however can account for a varying degree of background absorption by appropriate selection of the anisotropy factor g, depending on the spectral region considered. Appropriate values can be found analytically or experimentally. The expression for $\alpha$ is found from Eq. (4) and Eq. (3) as:

$$\alpha = 1 - \frac{4}{5}\frac{\mu'_s + \mu_a}{\mu'_s(1+g) + \mu_a} \quad (5)$$

Typical values of $\alpha$ range from 0.2 to 0.6. For visible light propagating in biological tissue, $\alpha$ is on the order of 0.50 to 0.55, assuming an anisotropy factor of g~0.8, which is typical for biological tissue. The dependence of $\alpha$ with g is small, and changes in the value of g within realistic biological values (g between 0.5 and 0.9) give small changes in the value of $\alpha$.

It will be understood that if a conventional diffusion coefficient is used (i.e., with $\alpha=0$ or $\alpha=1$), the diffusion approximation yields inaccurate results for a medium with high absorption. This is the reason why it has been long been thought that the diffusion approximation fails in the presence of high absorption (e.g., for visible light propagating in biological tissue). However, when the modified diffusion coefficient of equation 4 is used, the diffusion approximation remains accurate. To that end, a modified wavenumber must be defined as:

$$k^\lambda = \sqrt{-\frac{\mu_a^\lambda}{D_a^\lambda} + \frac{i\omega}{vD_a^\lambda}} \quad (6)$$

where $\omega$ is the modulation frequency ($\omega=0$ for continuous wave excitation light). Combining the modified diffusion coefficient of equation 4 with the wave propagation wavenumber of equation 6, Green's function solutions to the diffusion approximation can be derived that are appropriate for imaging in the presence of high absorption, e.g., for visible light propagating in biological tissue.

The above described model (Eq. 1 and subsequent explanatory equations) can make use of properties of the apparent light sources, for example, their position and intensities.

At block 214, the first image information, the second image information, and the light propagation model are combined, for example, in a so-called "forward model." Where the specimen has internal fluorescent proteins and is therefore not internally homogeneous, the combining of block 214 generates an "image problem" or "forward model" of the form: measurements=(theoretical predictions)×(unknown distribution), where the measurements are provided at blocks 204-210 by the light detector 32 (FIG. 1) and the theoretical predictions are provided at block 212 by the image processor 34 (FIG. 1), generally in accordance with equations (1)-(6). The unknown distribution corresponds to the fluorescent light emitted by the fluorescent proteins. The image processor 34 can solve for the unknown distribution in order to establish physical positions and characteristics of the fluorescent proteins 20 (FIG. 1) in the specimen 18 (FIG. 1).

At block 216, a map is generated of the fluorescent protein concentration in the specimen. In some embodiments, the map is a tomographic image. To generate the map, the above-described forward model is "inverted" to solve for the above-described unknown distribution.

In generating the fluorescent protein map, the volume of interest can be segmented into axial (horizontal) layers (e.g., 21 layers) each containing a number (e.g., 651) of voxels. The voxel size is selected based upon the dimension of the field of view and the number of segmentations.

The volume of interest can be segmented in a number of voxels in three dimensions. These can be seen as horizontal, vertical, or transverse layers, resembling cubes stacked next to each other in three dimensions. Each of the voxels has an unknown amount of fluorescent proteins and an unknown attenuation. If the fluorescence and attenuation in each of the voxels were known, the measured images could be predicted. However the fluorescence and attenuation in each voxel are not known. Therefore the above-described forward problem can be solved (inverted) to find the map of the fluorescent proteins.

It may be desirable, in some embodiments, to superimpose a white light image of the specimen onto the map of the fluorescent protein concentration, in order to give enhanced understandability of the image. To this end, the specimen can be illuminated by a white light source at block 218 and a white light can be received at block 220 and a white light image can be generated at block 222.

The white light image generated at block 222 can be superimposed at block 224 with the fluorescent protein map generated at block 216. To this end, in one particular embodiment, the white light image is registered or aligned with the map of the fluorescent proteins.

In order to align the white light image with the map of the fluorescent proteins, an image of the apparent light sources can be made, for example, through a phantom, to allow the apparent light source coordinates to be determined. This procedure improves the co-registration of a white light image that can be superimposed upon tomographic images, reducing relative positional errors.

Figure 5:
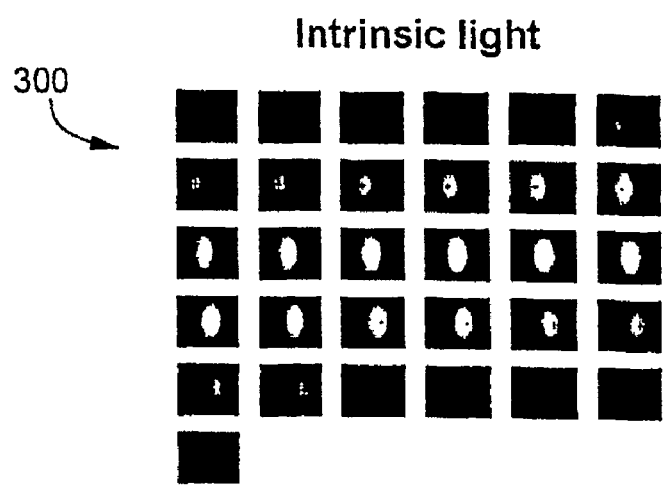
FIG. 5 shows a series of thirty-one images, corresponding to the thirty-one apparent light sources of FIG. 1 as provided by the optical scanner of FIG. 3, showing intrinsic light (i.e., excitation light from the apparent light sources having entered and exited a specimen)

Referring now to FIG. 5, thirty-one images 300 of intrinsic light correspond to thirty-one apparent light sources directing light at a specimen and intrinsic light received as transillumination light therefrom. The apparent light sources direct light at the specimen either one at a time or at the same time, or in any combination.

The images 300 can be generated using a bandpass interference filter (e.g., 28, FIG. 1) centered on the wavelength of the excitation light from the light source (e.g., 12, FIG. 1).

Figure 5A:
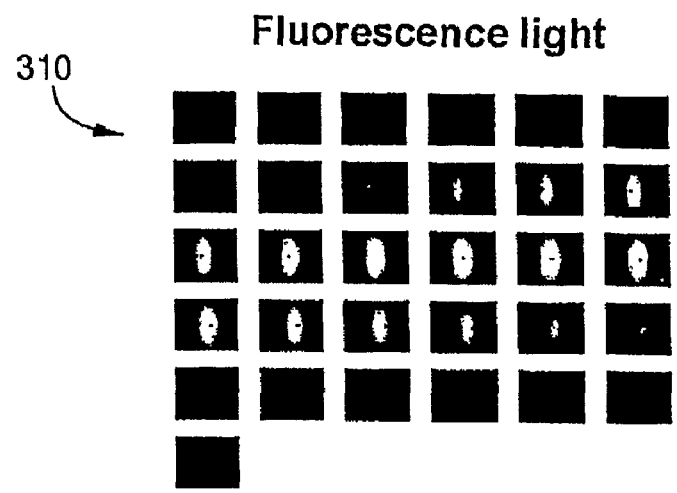
FIG. 5A shows another series of thirty-one images, corresponding to the thirty-one apparent light sources of FIG. 1 as provided by the optical scanner of FIG. 3, showing fluorescent light emitted from fluorescent proteins within a specimen in response to the intrinsic light of FIG. 5.

Referring now to FIG. 5A, thirty-one images 310 of fluorescent light correspond to the thirty-one apparent light sources directing light at a specimen and emitted fluorescent light received therefrom. The apparent light sources direct light at the specimen either one at a time or at the same time, or in any combination. The fluorescent light can be received either while the apparent light sources are directing light at the specimen or after the apparent light sources direct light at the specimen. The intrinsic light images of FIG. 5 and the fluorescent light images of FIG. 5A are combined, for example at block 214 of FIG. 4.

The images 310 can be generated using a band-pass interference filter (e.g., 28, FIG. 1) centered on the wavelength of the emitted light from the fluorescent proteins (e.g., 20, FIG. 1).

The measurements (or images) 300, 310 are used to generate the field $U_c(\vec{r}_s, \vec{r}_d)$ described by Eq. (1). Exposure times can be varied between individual images so that dynamic range is maximized.

Figure 5B:
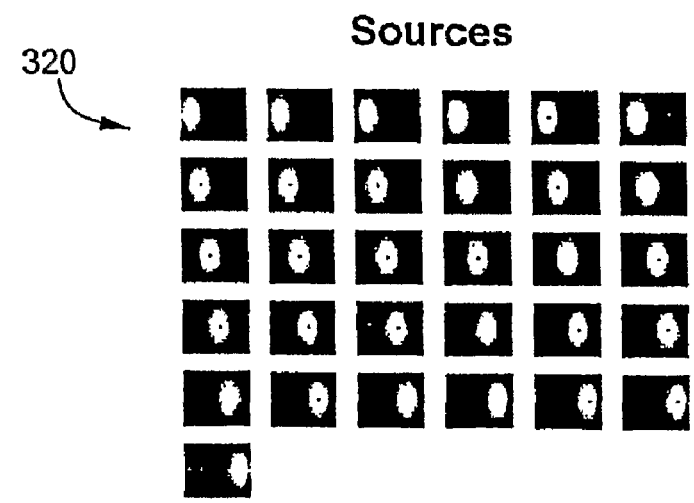
FIG. 5B shows yet another a series of thirty-one images, corresponding to the thirty-one apparent light sources of FIG. 1 as provided by the optical scanner of FIG. 3, showing the transmitted light not having passed though the specimen, but having passed through a homogeneous slab (i.e., a phantom)

Referring now to FIG. 5B, thirty-one images 320 of the apparent light sources correspond to the thirty-one apparent light sources directing light through a phantom and light received therefrom. The apparent light sources direct light at the phantom either one at a time or at the same time, or in any combination. The images of the apparent light sources are used optionally, for example, to register a white light image with a map of fluorescent protein concentration as shown at block 224 of FIG. 4.

The images 320 can be generated using a band-pass interference filter (e.g., 28, FIG. 1) centered on the wavelength of the excitation light from the white light source (e.g., 40, FIG. 1).

Figure 6:
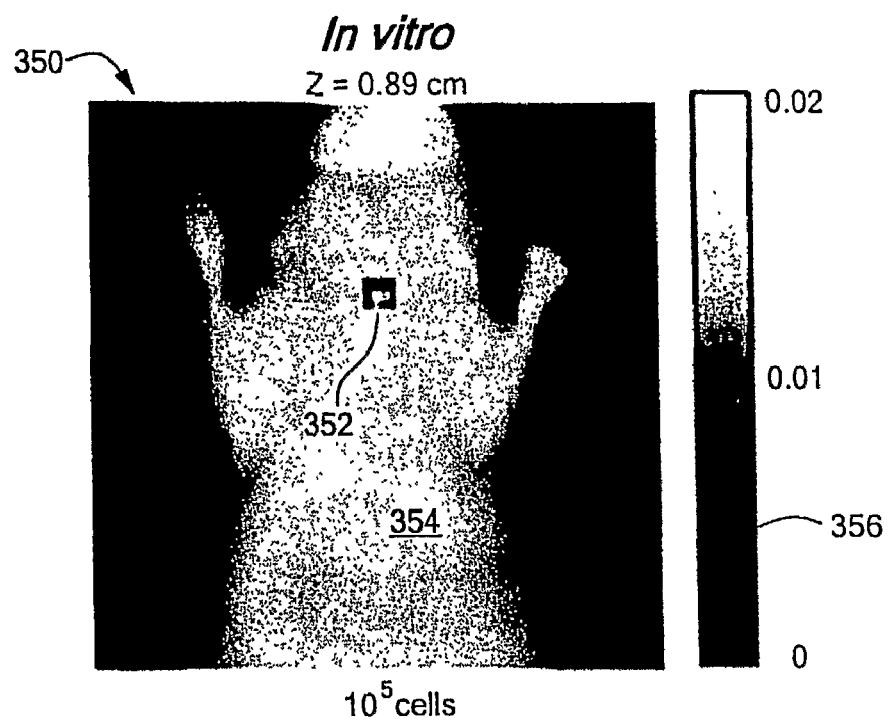
FIG. 6 shows a fluorescence image superimposed with a white light image of a dead mouse having a glass vial with green fluorescent protein (GFP) expressing cells placed into the esophagus.
Figure 6A:
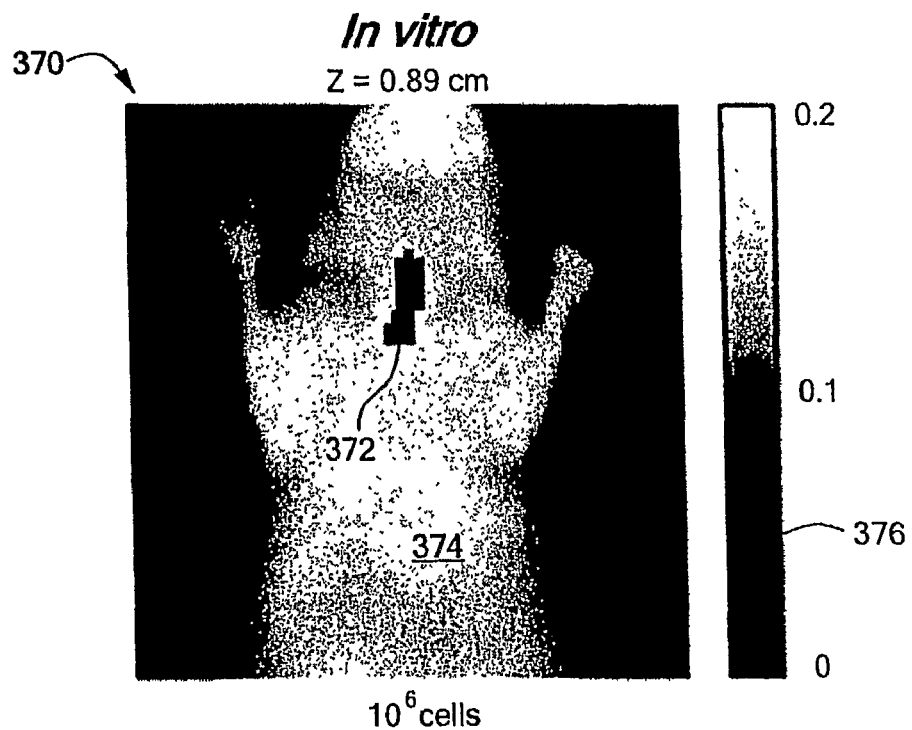
FIG. 6A shows another fluorescence image superimposed with a white light image of a dead mouse having another glass vial with green fluorescent protein (GFP) expressing cells placed into the esophagus, the glass vial having a higher number of cells than the vial of FIG. 6.

Referring now to FIGS. 6 and 6A, an example of images provided by the method and system of the present invention is shown. Two different numbers of green fluorescent protein (GFP) expressing tumor cells were used: $10^5$ and $10^6$. The fluorescent proteins were placed inside thin glass tubes and inserted in the esophagus of animals after they had been sacrificed. The animals were placed inside the imaging chamber (e.g., 16, FIG. 1), which was then filled with the matching fluid described above. Imaging was performed using the 31 apparent light source array transilluminating the area around the chest of the animal.

Referring first to FIG. 6, an image 350 includes a map 352 of the $10^5$ fluorescent proteins, upon which a white light image 354 of a mouse is superimposed.

Referring next to FIG. 6A, an image 370 includes a map 372 of $10^6$ fluorescent proteins, upon which a white light image 374 of the mouse is superimposed.

Figure 7:
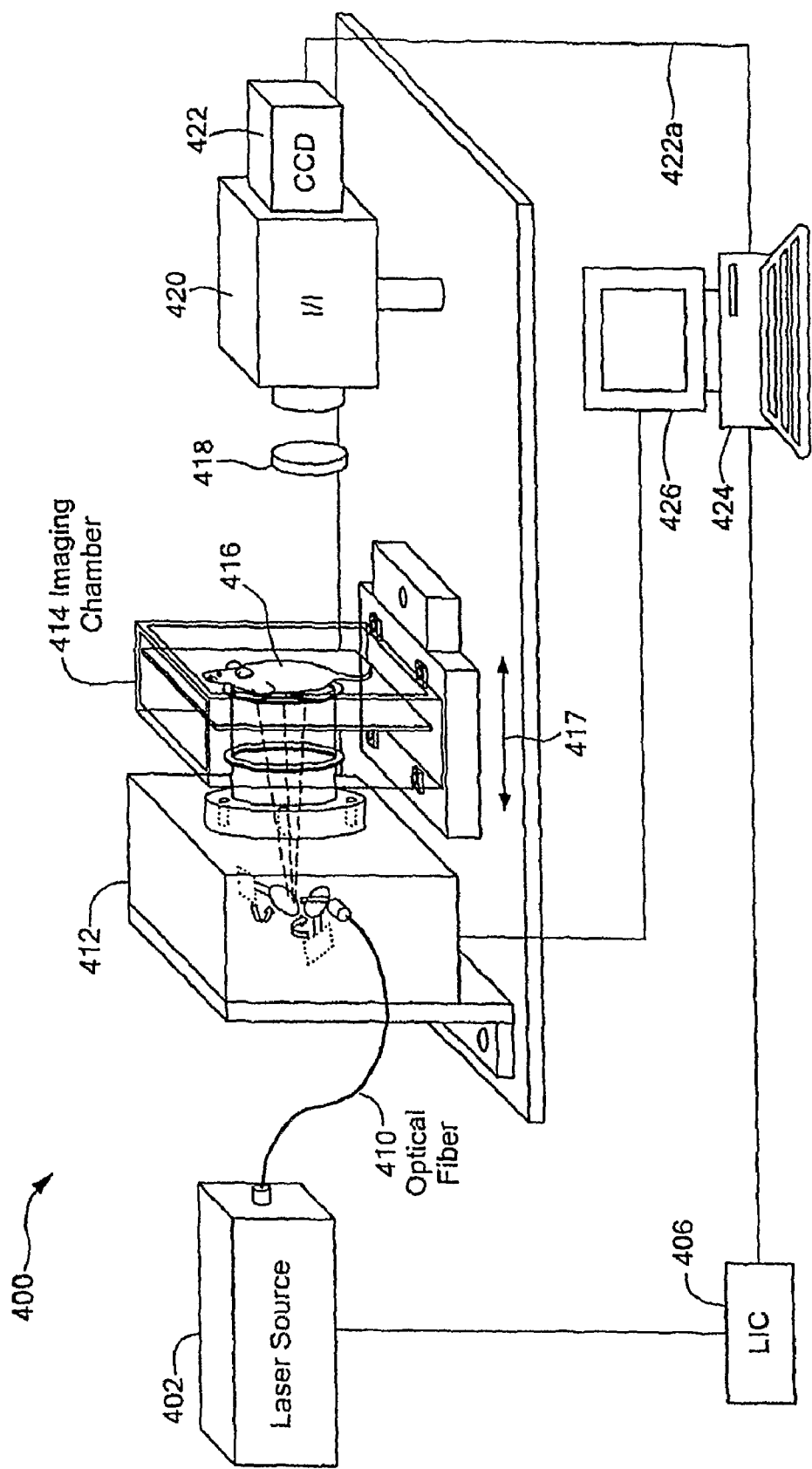
FIG. 7 is a block diagram of a system for optical tomography having a planar imaging chamber.

Referring now to FIG. 7, a system 400 for optical tomography 400 includes a laser source 402 coupled to an optical scanner 412, which provides a plurality of apparent light sources, as described, for example, in conjunction with FIG. 3. The system 400 also includes a laser intensity controller 406 (LIC). The LIC 406 provides intensity control to the laser source 402.

The system 400 further includes an image intensifier 420 and a CCD camera. A selectable light filter 418 is selectively band centered at the wavelength of the excitation light transmitted by the apparent light sources or at the wavelength of the light emitted by fluorescent proteins within a specimen 416. A computer 424 can control the LIC 406 and the optical scanner 412. The computer can also function as an image processor, for example, as the image processor 34 of FIG. 1, providing images on a graphical display 426.

In operation, the optical scanner 412 provides a plurality of apparent light sources at a corresponding plurality of positions relative to the specimen 416. The CCD camera collects both intrinsic light passing though the specimen 416 as transillumination light and also fluorescent light emitted by fluorescent proteins within the specimen 416. The CCD camera converts the received light into digital data, which the computer processes as described above in conjunction with FIG. 4, to provide a tomographic image on the graphical display 426.

In this particular embodiment, a plurality of images necessary for tomographic imaging are associated with positions of the plurality of apparent light sources provided by the optical scanner 412, and the imaging chamber remains substantially stationary, but can be moved along an axis 417 to affect image quality.

Figure 7A:
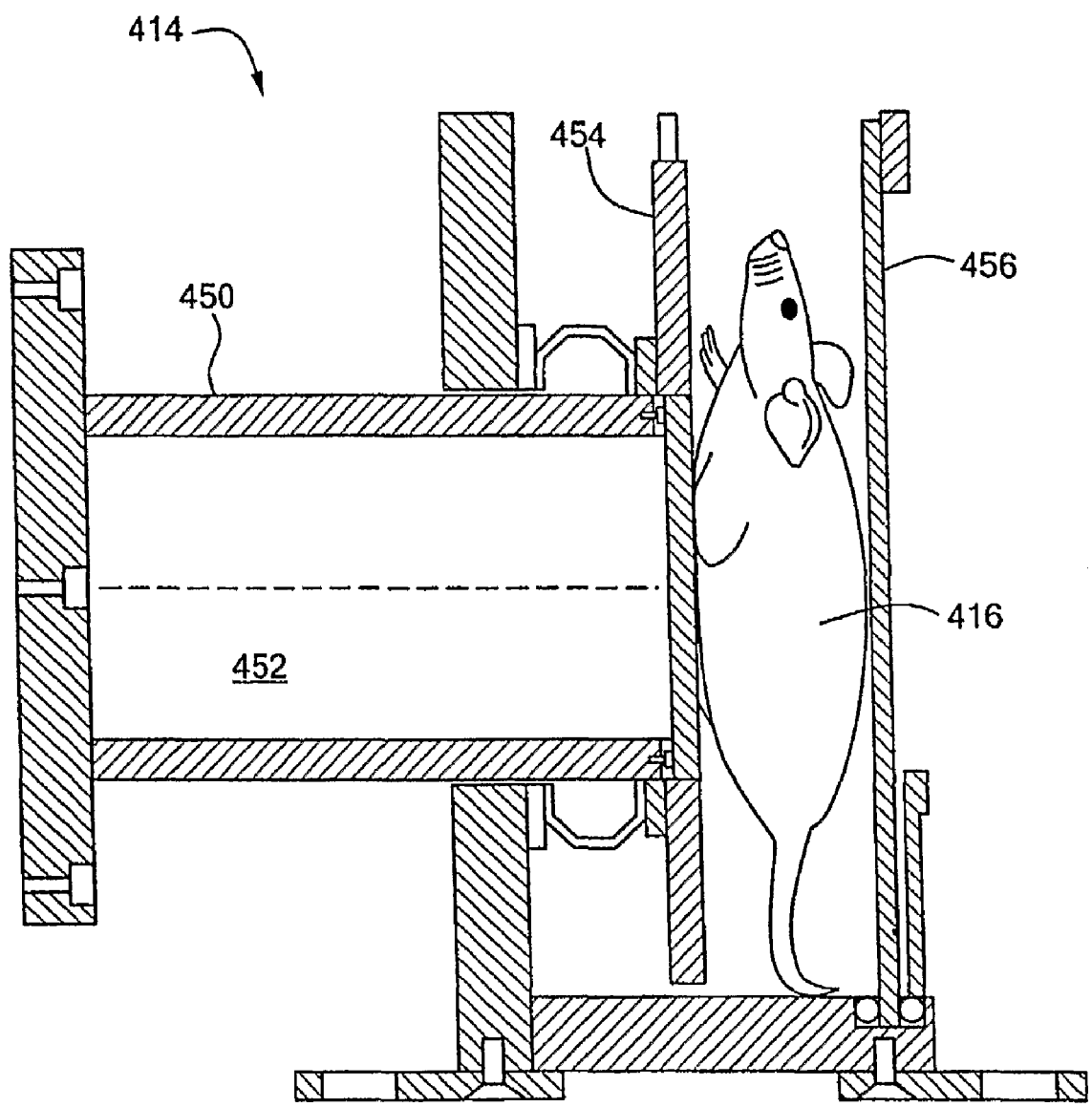
FIG. 7A is a block diagram showing an imaging chamber used in the system of FIG. 7.

Referring now to FIG. 7A, the imaging chamber 414 of FIG. 7 includes a cylinder 450, which can be filled with a matching fluid as described, for example, in conjunction with FIG. 2. An imaging plate 454 and a cover glass 456 surround the specimen 416.

Figure 8:
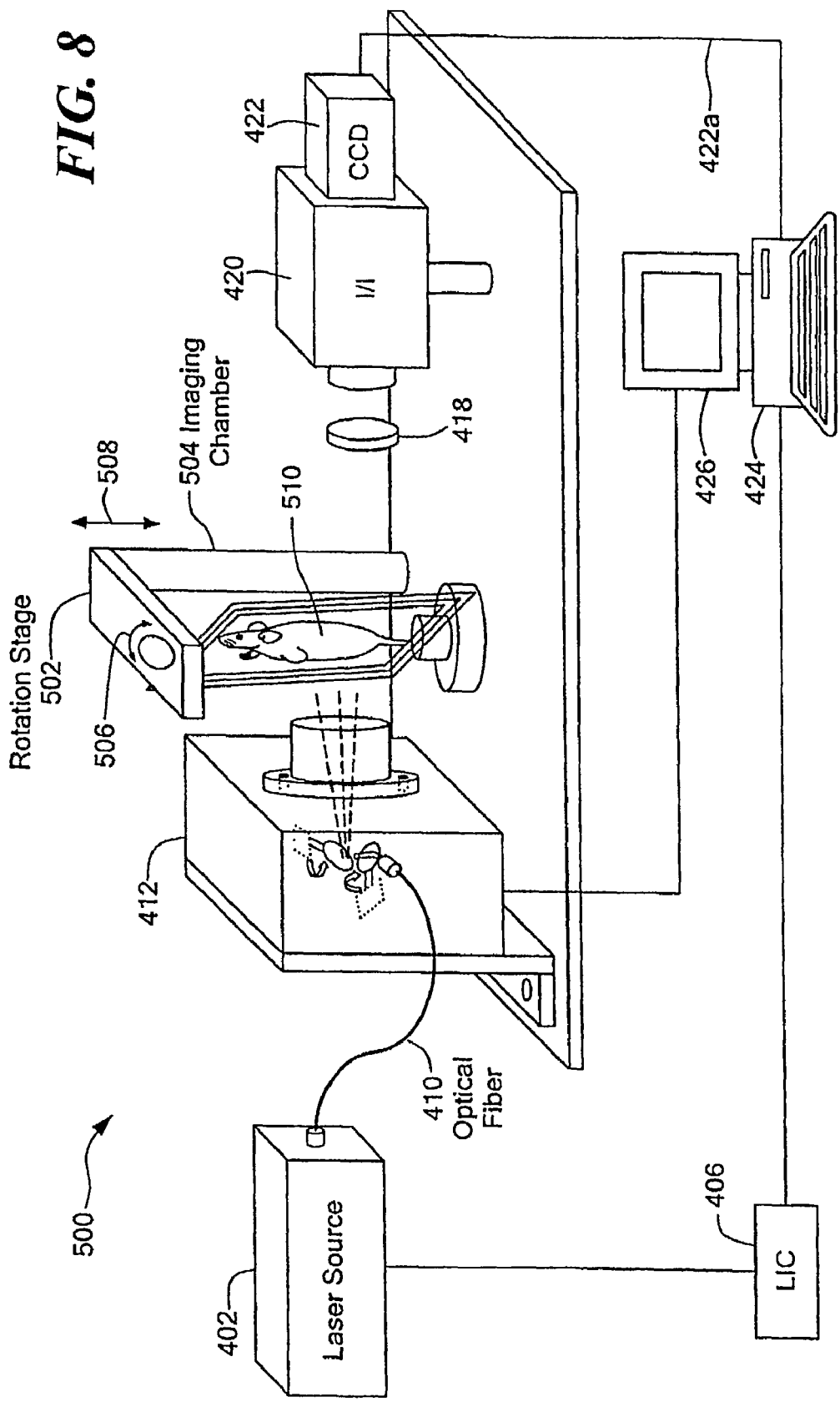
FIG. 8 is block diagram of an alternate system for optical tomography having a rotating planar imaging chamber.

Referring now to FIG. 8, in which like elements of FIG. 7 are shown having like reference designations, a system 500 for optical tomography includes an imaging chamber 504 holding a specimen 510. The imaging chamber 504 is adapted to rotate as represented by an arrow 506 and to move in translation along an axis 508. The system 500 can include a rotation stage 502 to hold the imaging chamber 504.

As described in conjunction with FIG. 7, a plurality of images necessary for tomographic imaging is associated with positions of the plurality of apparent light sources provided by the optical scanner 412. In addition, the imaging chamber 504 can be moved in rotation and in translation, for example, under control of computer 424, to provide further apparent light source positions and/or angles, to provide further images of the specimen 510.

Figure 8A:
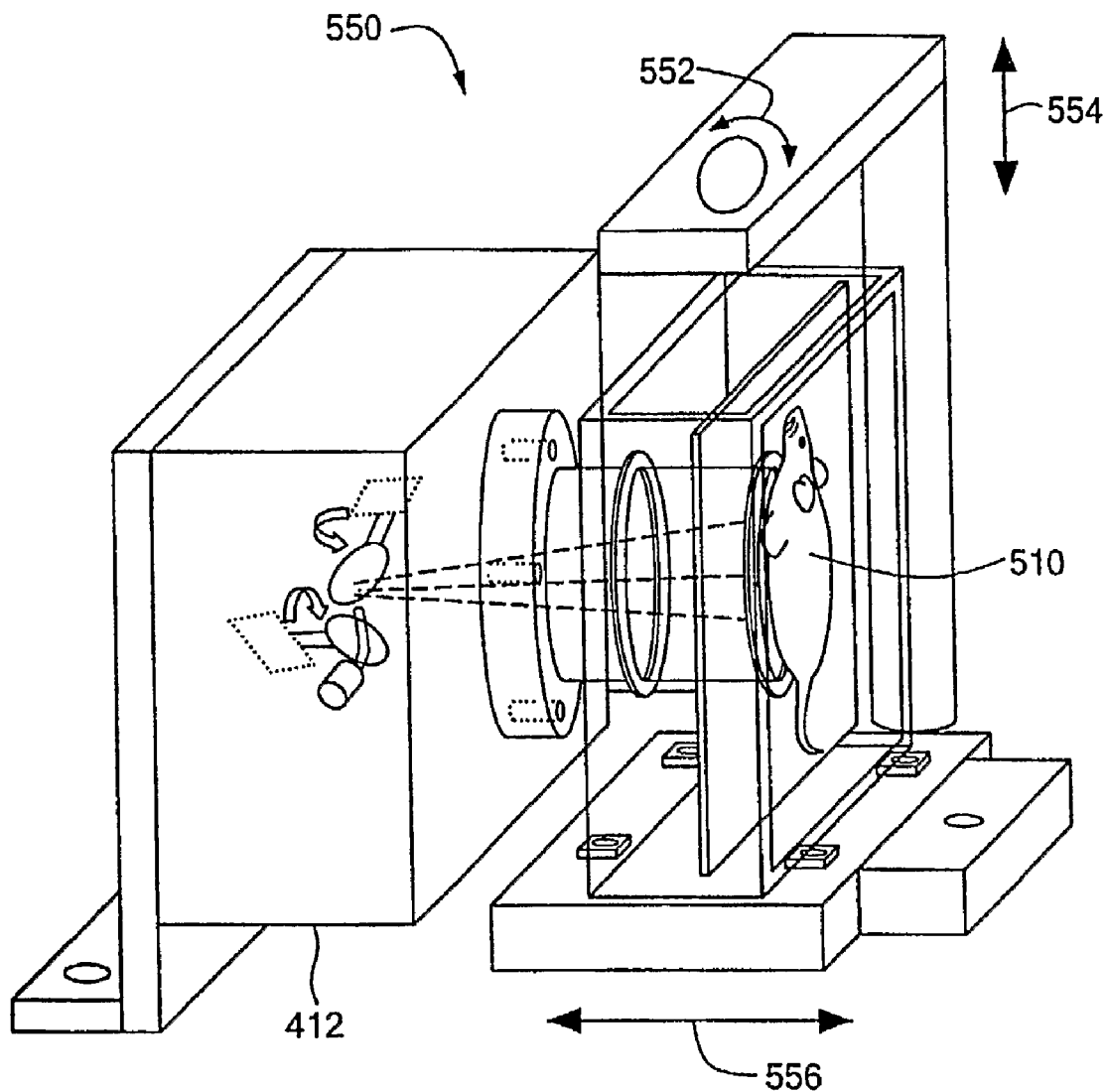
FIG. 8A is block diagram of a rotating planar imaging chamber that can be used in the system of FIG. 8.

Referring now to FIG. 8A, in which like elements of FIGS. 7 and 8 are shown having like reference designations, the imaging chamber 504 of FIG. 8 can be replaced with an imaging chamber 550 as shown, for example in FIG. 7A, but adapted to move in rotation as represented by an arrow 552 and to move in translation as represented by an arrow 554.

The imaging chamber 550 is also able to move in translation along an axis represented by and arrow 556, which allows for images obtained by the CCD camera 442 of FIG. 8 to be affected.

Referring now to FIG. 9, another system for optical tomography 600, in which like elements of FIG. 7 are shown having like reference designations, includes a generally cylindrical imaging chamber 602 in which a specimen 604 is placed. The imaging chamber 602 can rotate as represented by an arrow 606. The rotation can be computer controlled, for example, with a rotation stage controller 612 controlled by a computer 608. The LIC 406, FIG. 7 is not shown but can be included in the system 600.

As described in conjunction with FIG. 7, a plurality of images necessary for tomographic imaging is associated with positions of the plurality of apparent light sources provided by the optical scanner 412. In addition, the imaging chamber 602 can be rotated, for example under computer control, i.e., to provide further apparent light source positions and/or angles, to provide further images of the specimen 604.

An advantage of the cylindrical imaging chamber 602 is that both the rotation as well as the imaging algorithm are simple and fast, without imposing drawbacks on the image quality.

Figure 10:
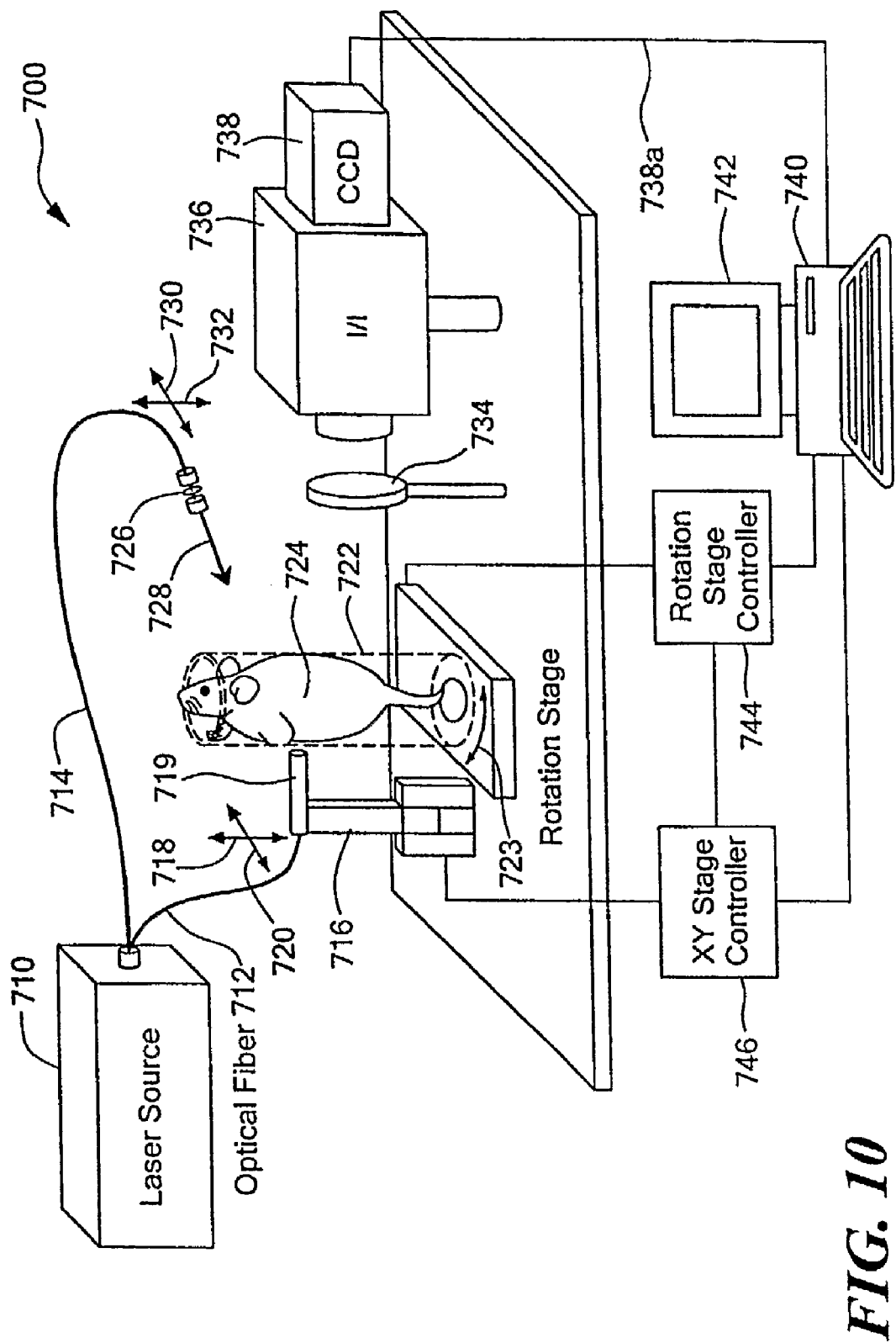
FIG. 10 is a block diagram yet another alternate system for optical tomography having a rotating cylindrical imaging chamber and a selectively movable apparent light source.

Referring now to FIG. 10, yet another system 700 for optical tomography includes a laser source 710, which provides light to an optical fiber 712. The optical fiber 712 is selectively movable along at least two axes 718, 720, for example, by a structure 716. The system 700 can also include a generally cylindrical imaging chamber 722 in which a specimen 724 is placed. The imaging chamber 722 can rotate as represented by an arrow 723. The rotation can be computer controlled, for example, with a rotation stage controller 744 controlled by a computer 740. Furthermore, motion of the structure 716, which provides motion of the fiber 712 on the at least two axes 718, 720 can be computer controlled, for example, with an XY-stage controller 746 controlled by the computer 740. The LIC 406, FIG. 7 is not shown but can be included in the system 700.

As with the systems above, intrinsic light passing though the specimen 724 and fluorescent light emitted from within the specimen 724 pass through a selectable light filter 734 and are received by an image intensifier 736 and a CCD camera 738. The CCD camera provides digital data 738a to the computer 740, which provides at least the processes shown in blocks 208-216 of FIG. 4, and which provides a map of fluorescent proteins within the specimen 724 on a graphical display 742.

Another optical fiber 714 can provide a second light source 726 on the opposite side of the specimen 724 from the optical fiber 712. The second light source 726 can be a single white light source used to provide the white light image of blocks 218 to 224 of FIG. 4. In other embodiments, the second light source 726 can be selectively moved in at least two axes 730, 732 to provide another plurality of apparent light sources used in reflectance imaging of the specimen 724, in much the same way as shown, for example, in FIG. 1A.

The same high quality 3D images provided by the system 600 of FIG. 9 can be achieved with the system 700 of FIG. 10. However an advantage of the system 700 is that it can work in reflectance mode as well as transillumination mode and can implement any geometry, for example, a free-space (i.e., non-contact and no matching fluid) cylindrical geometry.

Figure 10A:
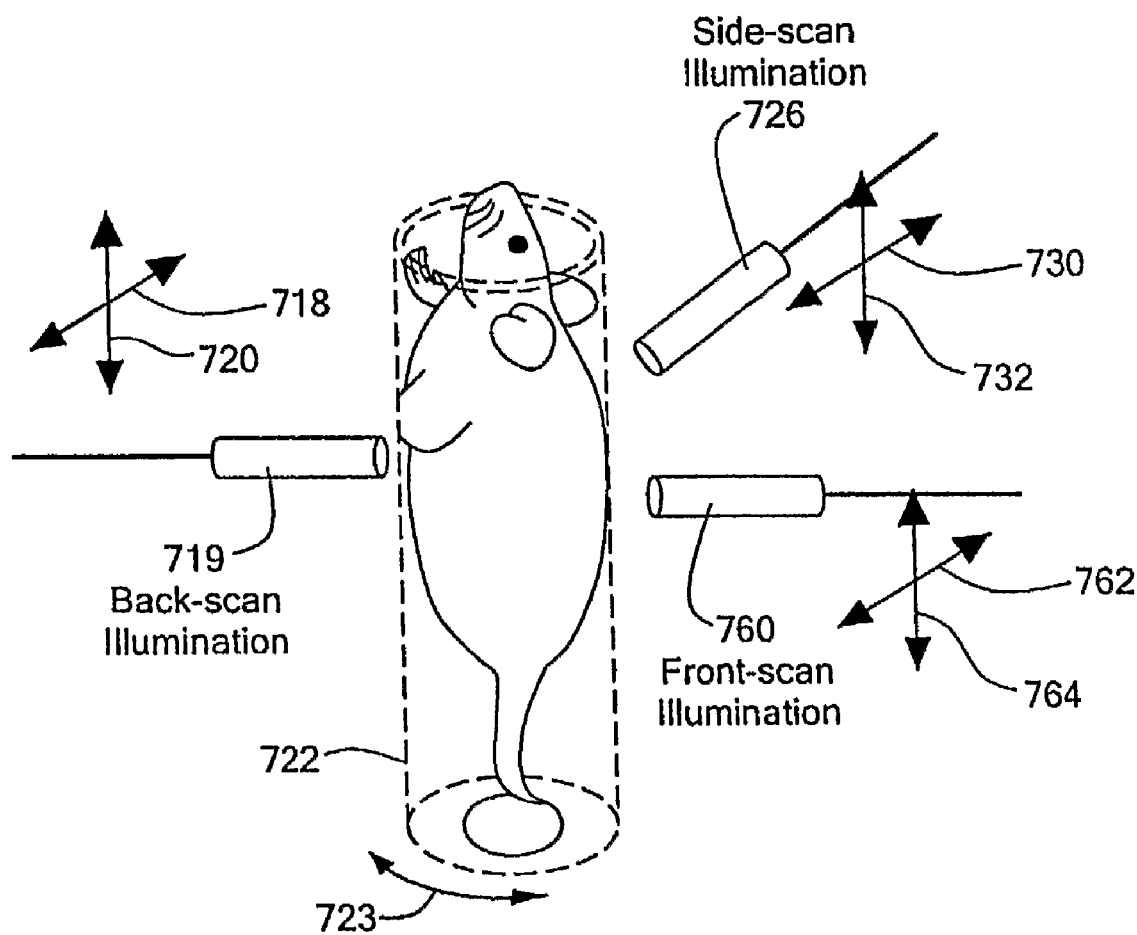
FIG. 10A is a block diagram showing a rotating cylindrical imaging chamber and a plurality of light sources.

Referring now to FIG. 10A, in which like elements of FIG. 10 are shown having like reference designations, a third light source 760 can be provided to achieve even more apparent light sources. In some embodiments, the third light source 760 is selectively moveable along at least two axes 762, 764, providing, for example, both side illumination with the second light source 726 and front illumination with the third light source 760.

Side illumination and front illumination can be used to improve the collection efficiency of low level light signals, especially signals otherwise hidden by large absorbers in transillumination mode using the first light source 719. Measurements resulting from the first, second and third light sources 719, 726, 760, respectively, can be combined with tomographic processing and used to solve a forward problem similar to that described above in conjunction with FIG. 4.

Figure 11:
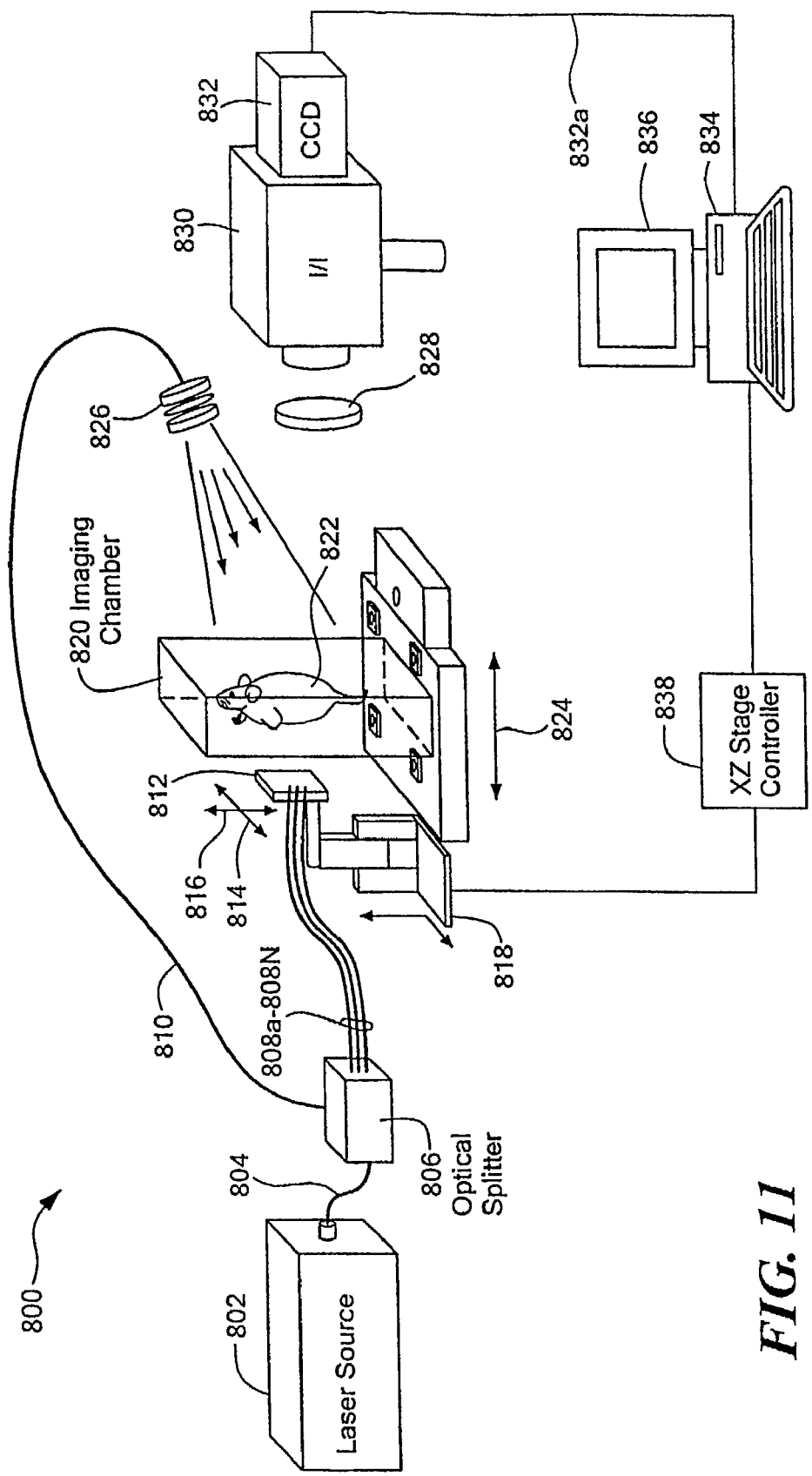
FIG. 11 is a block diagram yet another alternate system for optical tomography having an optical scanning head having array of apparent light sources.

Referring now to FIG. 11, another imaging system 800 includes a laser light source 802 to generate excitation light and a single optical fiber 804. The optical fiber 804 is coupled to an optical splitter 806, which spits the excitation light to a both a plurality of optical fibers 808a-808N and to an optical fiber 810, each carrying the excitation light. The optical fibers 808a-808N couple to a scanning head 812, which can move in translation along at least two axes represented by arrows 814, 816. In one particular embodiment, the optical fibers 808a-808N provide apparent light sources, which project excitation light at the same time toward a specimen 822 disposed within an imaging chamber 820 (or imaging chamber).

As with the systems described above, intrinsic light exiting the specimen 822 and also fluorescent light emitted by fluorescent proteins within the specimen 822 passes through a selectable filter 828, through an image intensifier 830, and into a CCD camera 832. The light is converted to digital data 832a by the CCD camera 832, which is received by a computer 834. The computer 834 processes the digital data as described, for example, by the process 200 of FIG. 4, and can present a graphical display of tomographic images on the graphical display 836.

A white light source 826 can generate white light, which reflects from the specimen 822, providing white light though the selectable filter 828, through the image intensifier 830, and into the CCD camera. As described in conjunction with FIG. 4, the white light image of the specimen 822 can be superimposed with a map of the fluorescent proteins within the specimen 822, resulting in a more understandable tomographic image.

The computer 834 can also control the position of the scanning head 812 via an XY stage controller 838, moving the scanning head about axes as represented by the arrows 814, 816 to provide more apparent light sources, resulting in a better tomographic map of the fluorescent proteins.

In one particular embodiment, the scanning heard 812 can be scanned along at least two axes represented by arrows 814, 816 and all of the optical fibers 808a-808N coupled to the scanning head 812 can be illuminated at the same time. Advantages of such an embodiment include, but are not limited to, faster tomographic imaging, particularly in the presence of low amplitude light signals, which result in long exposure times.

Crosstalk between the fibers 808a-808N can be minimized by appropriate selection of distances between the individual fibers 808a-808N so that the paths of the propagating photons do not overlap. In other embodiments, particularly those for which exposure times can be short, the fibers 808a-808N can be illuminated one at a time to eliminate noise from crosstalk between the fibers 808a-808N. In this embodiment the optical splitter 806 can be replaced by an optical switch, (e.g., 106, FIG. 2). In an alternate embodiment, a single fiber can be scanned along axes represented by arrows 814, 816.

Figure 11A:
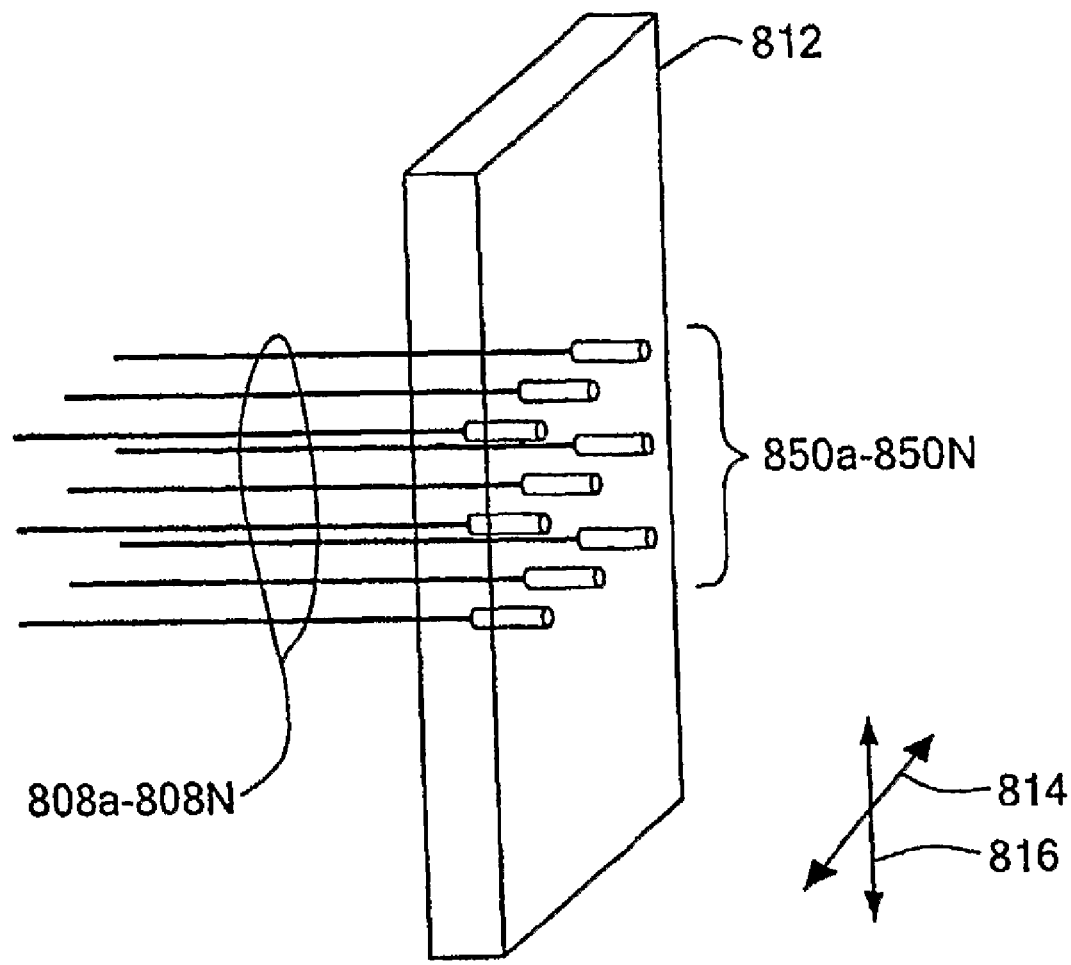
FIG. 11A is a block diagram of the optical scanning head as shown in FIG. 11.

Referring now to FIG. 11A, in which like elements of FIG. 11 are shown having like reference designations, the scanning head 812 of FIG. 11 has a plurality of apertures 850a-850N, each of which correspond to a respective apparent light source, forming N apparent light sources. When the scanning head 812 is moved along an axis, for example axes represented by arrows 814, 816, further apparent light sources are formed, for example, another N apparent light sources.

The method and system of the present invention can use any fluorescent proteins, including, but not limited to, DsRed and HcRed fluorescent proteins. These particular fluorescent proteins provide fluorescent light in the red or near-infrared region of the visible light spectrum. These particular fluorescent proteins can result in maps of fluorescent proteins having higher quality because the red region of the visible spectrum of light has a higher efficiency deep penetration depth in biological tissue compared with other wavelengths of visible light and can provide higher resolution than longer wavelength NIR systems.

The method and system of the present invention can be used for studying tumor growth and monitoring of metastasis formation when used with tumor cells that express fluorescent proteins (like GFP).

The method and system of the present invention can be used with GFP expressing tumor cells and YFP expressing viral cells for the study of gene delivery and gene therapy for specific patient targeted treatment.

The method and system of the present invention can also take advantage of imaging modalities using algorithms for imaging arbitrary geometries without the need matching fluids. The algorithms for modeling of light propagation and solving forward problems can be applied to all of the above system embodiments.

It should be appreciated that the method and system of the present invention, when using visible light, provides higher spatial resolution than conventional tomographic approaches using near-infrared (NIR) light.

The excitation light and resulting emitted fluorescent light provided by above-described embodiments of the present invention can be continuous wave (CW) light, intensity modulated (IM) or time-resolved (TR) light, or a combination of both. The method and system of the present invention can give information on the dynamics of the system as function of time, and the resulting image can be co-registered with an image obtained by another imaging method such as magnetic resonance imaging (MRI), computed tomography imaging (CT), ultrasound or bioluminescence imaging.

This above described system and method use a modified diffusion approximation, combined with appropriate normalization, which enables three-dimensional tomographic imaging of fluorescent proteins in-vivo in a visible wavelength range of at least 400 nm to 700 nm in a medium having a relatively high absorption coefficient (e.g., >0.3 cm$^{-1}$), i.e., which is diffuse. The modified diffusion approximation does not require the use of the more complex transport equation. Therefore the modified solutions obtain computational efficiency.

In some embodiments described above, non-contact tissue illumination and/or non-contact light reception is used, wherein the above-described apparent light sources and/or light detector are spaced apart from the specimen being scanned. In other embodiments, the apparent light sources and/or the light detector are placed in substantial contact with the specimen, The above-described method and system can be applied to a variety of biological and molecular processes by using a variety of different fluorescent proteins. For example, in various embodiments, fluorescent proteins can be used to monitor tumor growth, metastasis formation, gene expression, and therapeutic effects. In addition, the method and system can be used to provide non-invasive, whole-body molecular imaging to non-invasively yield information associated with activity at sub-cellular levels.

The method and system of the present invention can provide insight into specific molecular and biological abnormalities that form the basis of many diseases, e.g., cancer, tumor growth, and metastasis formation. The method and system can also be used to image angiogenesis since the high absorption of hemoglobin contrasts the vessels against the fluorescent background of the tumor cells. Furthermore, the method and system can be used to assess efficacy of novel targeted therapies at a molecular level. This, in turn, can have an impact on drug development, drug testing, and choosing appropriate therapies and therapy changes in a given patient. Still further, the method and system enable study of the genesis of diseases in the intact microenvironment of living systems. And, still further, the method and system are useful for testing novel gene delivery strategies. The imaging method and system allow acquisition of three-dimensional information much faster than is currently possible with time consuming and labor intensive conventional basic science techniques.

The method and system of the present invention have broad applications in a wide variety of biologic, immunologic, and gene therapies designed to promote the control and eradication of a variety of diseases including cancer, neurodegenerative, inflammatory, infectious, and other diseases. Furthermore, the method and system have broad applications for seamless disease detection and treatment in combined settings.

All references cited herein are hereby incorporated herein by reference in their entirety.

Having described preferred embodiments of the invention, it will now become apparent to one of ordinary skill in the art that other embodiments incorporating their concepts may be used. It is felt therefore that these embodiments should not be limited to disclosed embodiments, but rather should be limited only by the spirit and scope of the appended claims.

What is claimed is:
1. A system for optical tomography, comprising:
   an apparent light source configured to project excitation light toward a specimen having fluorescent proteins therein, wherein the excitation light enters the specimen becoming intrinsic light within the specimen, wherein the intrinsic light is configured to excite fluorescent light from the fluorescent proteins, and wherein at least one of the intrinsic light or the fluorescent light has a wavelength within a visible wavelength range, the visible wavelength range spanning from about 400 nanometers to about 700 nanometers;
   a light detector configured to receive the intrinsic light exiting the specimen and configured to receive the fluorescent light exiting the specimen; and
   an image processor coupled to the light detector and configured to use a light propagation model, wherein the light propagation model is configured to predict propagation of visible light in a diffuse medium, wherein the image processor comprises a diffusion equation processor configured to use a diffusion equation having a modified diffusion coefficient selected in accordance with the propagation of visible light in the diffuse medium throughout a substantial portion of the visible wavelength range, wherein the modified diffusion coefficient has the form

$$D_\alpha = \frac{1}{3(\mu_s' + \alpha\mu_a)},$$

where $\alpha$ is a constant having a value depending on absorption, scattering, and anisotropy of the diffuse medium, $\mu_s'$ is a reduced scattering coefficient, and $\mu_a$ is an absorption coefficient.

2. The system of claim 1, wherein the intrinsic light and the fluorescent light are diffuse.

3. The system of claim 1, wherein the fluorescent light has a wavelength in the visible wavelength range and outside of a near infrared range.

4. The system of claim 1, wherein the fluorescent light has a wavelength in a red portion of the visible wavelength range.

5. The system of claim 1, wherein the fluorescent light has a wavelength in a near infrared range.

6. The system of claim 1, wherein the light detector is further configured to convert the received intrinsic light into first image information, and further configured to convert the received fluorescent light into second image information, and wherein the image processor is further configured to combine the first image information, the second image information, and the light propagation model, and further configured to provide a tomographic image of the fluorescent proteins.

7. The system of claim 6, wherein the light detector is selectively movable to receive the intrinsic light and fluorescent light on a plurality of light paths relative to the specimen.

8. The system of claim 6, further including an optical scanner to provide the intrinsic light and fluorescent light to the light detector on a plurality of light paths relative to the specimen.

9. The system of claim 1, wherein the apparent light source includes a light directing device to selectively move a projection direction of the apparent light source to direct the excitation light on a plurality of light paths toward the specimen.

10. The system of claim 9, wherein the light directing device includes an optical switch to selectively move the projection direction of the apparent light source to provide the plurality of light paths toward the specimen.

11. The system of claim 9, wherein the light directing device includes a movable mirror to selectively move the projection direction of the apparent light source to provide the plurality of light paths toward the specimen.

12. The system of claim 9, wherein the light directing device is configured to selectively move the projection direction of the apparent light source in translation along at least one apparent light source translation axis.

13. The system of claim 1, wherein the specimen is selectively movable to provide the excitation light on a plurality of light paths relative to the specimen.

14. The system of claim 13, wherein the specimen is selectively movable in rotation about a specimen rotation axis.

15. The system of claim 13, wherein the specimen is selectively movable in translation along at least one specimen translation axis.

16. The system of claim 13, wherein the specimen is selectively movable in rotation about a specimen rotation axis and the specimen is further selectively moveable in translation along at least one specimen translation axis.

17. The system of claim 1, wherein the apparent light source includes a light directing device to selectively move a projection direction of the apparent light source to direct the excitation light on a plurality of light paths toward the specimen and the specimen is selectively movable to provide the excitation light on a plurality of light paths relative to the specimen.

18. The system of claim 1, wherein the intrinsic light passes through the specimen as transillumination light.

19. The system of claim 1, wherein the intrinsic light reflects from the specimen as reflectance light.

20. The system of claim 1, wherein at least one of the intrinsic light or the emitted light propagate through the specimen a distance of at least 0.5 mm.

21. The system of claim 1, wherein the intrinsic light has a wavelength in the visible wavelength range and outside of a near infrared range.

22. The system of claim 1, wherein the modified diffusion coefficient is selected in accordance with the propagation of visible light in the diffuse medium down to a smallest wavelength of about 400 nanometers.

23. A method of optical tomography, comprising:

generating excitation light with an apparent light source configured to project the excitation light toward a specimen having fluorescent proteins therein, wherein the excitation light enters the specimen becoming intrinsic light within the specimen, wherein the intrinsic light is configured to excite fluorescent light from the fluorescent proteins, and wherein at least one of the intrinsic light or the fluorescent light has a wavelength within a visible wavelength range, the visible wavelength range spanning from about 400 nanometers to about 700 nanometers;

receiving the intrinsic light exiting the specimen;

receiving the fluorescent light exiting the specimen; and analyzing the at least one of the intrinsic light or the emitted light with a light propagation model configured to predict propagation of visible light in a diffuse medium, wherein the light propagation model is configured to predict the propagation of the visible light having a wavelength in the visible wavelength range, wherein the light propagation model is generated in accordance with a solution to a diffusion equation having a modified diffusion coefficient selected in accordance with the propagation of visible light in the diffuse medium throughout a substantial portion of the visible wavelength range; wherein the modified diffusion coefficient has the form $$D_\alpha = \frac{1}{3(\mu_s' + \alpha\mu_a)}$$

where $\alpha$ is a constant having a value depending on absorption, scattering, and anisotropy of the diffuse medium, $\mu_s'$ is a reduced scattering coefficient, and $\mu_a$ is an absorption coefficient.

24. The method of claim 23, wherein the intrinsic light and the fluorescent light are diffuse.

25. The method of claim 23, wherein the fluorescent light has a wavelength in the visible wavelength range and outside of a near infrared range.

26. The method of claim 23, wherein the fluorescent light has a wavelength in a red portion of the visible wavelength range.

27. The system of claim 23, wherein the fluorescent light has a wavelength in a near infrared range.

28. The method of claim 23, further comprising:

converting the received intrinsic light into first image information;

converting the received fluorescent light into second image information; and combining the first image information, the second image information, and the light propagation model to provide a tomographic image of the fluorescent proteins.

29. The method of claim 28, wherein the receiving the intrinsic light and the receiving the fluorescent light include receiving the intrinsic light and receiving the fluorescent light with a selectively movable light detector configured to receive the intrinsic light and fluorescent light on a plurality of light paths relative to the specimen.

30. The method of claim 23, further comprising selectively moving a projection direction of the apparent light source to direct the excitation light on a plurality of light paths toward the specimen.

31. The method of claim 30, wherein the apparent light source includes an optical switch to selectively move the projection direction of the apparent light source.

32. The method of claim 30, wherein the apparent light source includes a selectively movable mirror to selectively move the apparent light source.

33. The method of claim 30, wherein the selectively moving the projection direction of the apparent light source includes selectively moving the projection direction of the apparent light source in translation along at least one apparent light source translation axis.

34. The method of claim 23, further comprising selectively moving the specimen to provide the excitation light on a plurality of light paths relative to the specimen.

35. The method of claim 34, wherein the selectively moving the specimen includes selectively moving the specimen in rotation about a specimen rotation axis.

36. The method of claim 34, wherein the selectively moving the specimen includes selectively moving the specimen in translation along at least one specimen translation axis.

37. The method of claim 34, wherein the selectively moving the specimen includes:
 selectively moving the specimen in rotation about a specimen rotation axis; and
 selectively moving the specimen in translation along at least one specimen translation axis.

38. The method of claim 23, further comprising:
 selectively moving a projection direction of the apparent light source to direct the excitation light on a plurality of light paths toward the specimen; and
 selectively moving the specimen to provide the excitation light on another plurality of light paths relative to the specimen.

39. The method of claim 23, wherein the intrinsic light passes through the specimen as transillumination light.

40. The method of claim 23, wherein the intrinsic light reflects from the specimen as reflectance light.

41. The method of claim 23, wherein at least one of the intrinsic light or the emitted light propagate through the specimen a distance of at least 0.5 mm.

42. The method of claim 23, wherein the intrinsic light has a wavelength in the visible wavelength range and outside of a near infrared range.

43. The method of claim 23, wherein the modified diffusion coefficient is selected in accordance with the propagation of visible light in the diffuse medium down to a smallest wavelength of about 400 nanometers.

* * * * *

UNITED STATES PATENT AND TRADEMARK OFFICE
CERTIFICATE OF CORRECTION

| | |
|---|---|
| PATENT NO. | : 7,804,075 B2 |
| APPLICATION NO. | : 10/598703 |
| DATED | : September 28, 2010 |
| INVENTOR(S) | : Vasilis Ntziachristos et al. |

It is certified that error appears in the above-identified patent and that said Letters Patent is hereby corrected as shown below:

Col. 3, line 54, delete "another a series" and replace with --another series--.

Col. 3, line 57, delete "though" and replace with --through--.

Col. 4, line 12, delete "diagram yet" and replace with --diagram of yet--.

Col. 4, line 17, delete "diagram yet" and replace with --diagram of yet--.

Col. 4, lines 18-19, delete "having array" and replace with --having an array--.

Col. 11, line 64, delete "has been long been" and replace with --has long been--.

Col. 12, line 17, delete "above described" and replace with --above-described--.

Col. 14, line 20, delete "though" and replace with --through--.

Col. 14, line 60, delete "and" and replace with --an--.

Col. 15, line 31, delete "though" and replace with --through--.

Col. 16, line 7, delete "to a" and replace with --to--.

Col. 16, line 27, delete "though" and replace with --through--.

Col. 16, line 39, delete "heard" and replace with --head--.

Col. 17, line 37, delete "above described" and replace with --above-described--.

Signed and Sealed this
Twenty-ninth Day of March, 2011

David J. Kappos
*Director of the United States Patent and Trademark Office*